United States Patent
Smith et al.

(10) Patent No.: US 8,466,228 B2
(45) Date of Patent: *Jun. 18, 2013

(54) SUPERABSORBENT POLYMER WITH HIGH PERMEABILITY

(75) Inventors: Scott J. Smith, Düsseldorf (DE); Mark C. Joy, Reidsville, NC (US); Whei-Neen Hsu, Greensboro, NC (US); Markus Frank, Kuppenheim (DE); Michael M. Azad, Reidsville, NC (US)

(73) Assignee: Evonik Corporation, Parsippany, NJ (US)

(*) Notice: Subject to any disclaimer, the term of this patent is extended or adjusted under 35 U.S.C. 154(b) by 162 days.

This patent is subject to a terminal disclaimer.

(21) Appl. No.: 12/851,664

(22) Filed: Aug. 6, 2010

(65) Prior Publication Data

US 2010/0311578 A1  Dec. 9, 2010

Related U.S. Application Data

(63) Continuation of application No. 11/562,760, filed on Nov. 22, 2006, now Pat. No. 7,795,345, which is a continuation of application No. 10/424,195, filed on Apr. 25, 2003, now Pat. No. 7,169,843.

(51) Int. Cl.
*C08F 220/06* (2006.01)

(52) U.S. Cl.
USPC ........... 524/556; 524/430; 524/431; 524/442; 526/317.1; 526/240; 526/318.2

(58) Field of Classification Search
USPC ............... 524/430, 431, 442; 526/317.1, 240, 526/318.2
See application file for complete search history.

(56) References Cited

U.S. PATENT DOCUMENTS

| | | | |
|---|---|---|---|
| 4,771,105 A * | 9/1988 | Shirai et al. | 525/54.23 |
| 5,760,080 A * | 6/1998 | Wada et al. | 524/559 |
| 5,989,466 A | 11/1999 | Kato et al. | |
| 6,001,911 A * | 12/1999 | Ishizaki et al. | 524/388 |
| 6,245,252 B1 | 6/2001 | Hicks et al. | |
| 6,265,488 B1 * | 7/2001 | Fujino et al. | 525/119 |
| 6,565,981 B1 | 5/2003 | Messner et al. | |
| 6,727,345 B2 * | 4/2004 | Kajikawa et al. | 528/502 R |
| 6,906,131 B2 | 6/2005 | Ahmed et al. | |
| 7,163,966 B2 | 1/2007 | Joy et al. | |
| 7,163,969 B2 | 1/2007 | Ahmed et al. | |

(Continued)

FOREIGN PATENT DOCUMENTS

| | | |
|---|---|---|
| CA | 2460152 A1 | 3/2003 |
| CN | 1568347 | 1/2005 |

(Continued)

OTHER PUBLICATIONS

Frank, U.S. Appl. No. 12/789,644, filed May 28, 2010.

(Continued)

*Primary Examiner* — Satya Sastri
(74) *Attorney, Agent, or Firm* — Smith Moore Leatherwood LLP; Philip P. McCann

(57) ABSTRACT

The invention relates to absorptive, crosslinked polymers which are based on partly neutralized, monoethylenically unsaturated monomers carrying acid groups, and have improved properties, in particular in respect of their capacity for transportation of liquids in the swollen state, and which has a high gel bed permeability and high centrifuge retention capacity.

21 Claims, 4 Drawing Sheets

U.S. PATENT DOCUMENTS

| | | | |
|---|---|---|---|
| 7,169,843 B2 * | 1/2007 | Smith et al. ............... | 524/556 |
| 7,241,280 B2 | 7/2007 | Christon et al. | |
| 7,241,820 B2 | 7/2007 | Smith et al. | |
| 7,291,674 B2 | 11/2007 | Kang et al. | |
| 7,312,286 B2 | 12/2007 | Lang et al. | |
| 7,335,713 B2 | 2/2008 | Lang et al. | |
| 7,399,813 B2 | 7/2008 | Lang et al. | |
| 7,427,650 B2 | 9/2008 | Smith et al. | |
| 7,482,058 B2 | 1/2009 | Ahmed et al. | |
| 7,488,541 B2 | 2/2009 | Ahmed et al. | |
| 7,579,402 B2 | 8/2009 | Ahmed et al. | |
| 7,615,579 B2 | 11/2009 | Joy et al. | |
| 7,776,984 B2 | 8/2010 | Frank | |
| 7,777,093 B2 | 8/2010 | Smith et al. | |
| 7,795,345 B2 * | 9/2010 | Smith et al. ............... | 524/556 |
| 2004/0214499 A1 | 10/2004 | Qin et al. | |
| 2005/0256469 A1 | 11/2005 | Qin et al. | |
| 2007/0135554 A1 | 6/2007 | McIntosh et al. | |
| 2007/0167560 A1 | 7/2007 | Smith et al. | |
| 2008/0009616 A1 | 1/2008 | Frank et al. | |
| 2008/0234420 A1 | 9/2008 | Smith et al. | |
| 2009/0023848 A1 | 1/2009 | Ahmed et al. | |
| 2009/0134357 A1 | 5/2009 | Bub et al. | |
| 2009/0191408 A1 | 7/2009 | Tian et al. | |
| 2010/0075844 A1 | 3/2010 | Loeker et al. | |
| 2010/0099781 A1 | 4/2010 | Azad et al. | |
| 2010/0100066 A1 | 4/2010 | Azad et al. | |
| 2010/0130355 A1 | 5/2010 | Tian et al. | |

FOREIGN PATENT DOCUMENTS

| | | |
|---|---|---|
| EP | 827753 A2 * | 3/1998 |
| EP | 1438354 A1 | 7/2004 |
| JP | 2002226599 A * | 8/2002 |
| WO | 03025054 A1 | 3/2003 |

OTHER PUBLICATIONS

Qin et al., U.S. Appl. No. 12/787,914, filed May 26, 2010.

Smith et al., U.S. Appl. No. 11/562,760, filed Nov. 22, 2006, Office Action dated Oct. 1, 2009.

Smith et al., U.S. Appl. No. 11/562,760, filed Nov. 22, 2006, Final Office Action dated Mar. 23, 2010.

Smith et al., U.S. Appl. No. 12/830,890, filed Jul. 6, 2010.

* cited by examiner

SUPERABSORBENT POLYMER WITH HIGH PERMEABILITY

This application is a continuation of U.S. application Ser. No. 11/562,760 filed Nov. 22, 2006, now U.S. Pat. No. 7,795,345 issued Sep. 14, 2010, which is a continuation of application Ser. No. 10/424,195, filed Apr. 25, 2003, now U.S. Pat. No. 7,169,843, issued Jan. 30, 2007, the disclosures of which are expressly incorporated herein by reference.

FIELD OF THE INVENTION

The invention relates to superabsorbent polymers which absorb water, aqueous liquids and blood wherein the superabsorbent polymers of the present invention have improved properties, in particular an improved relationship between gel bed permeability and fluid retention including achieving higher gel bed permeability without the disadvantages of low retention that are characteristic of higher gel strengths. The present invention also relates to preparation of these superabsorbent polymers and their use as absorbents in hygiene articles and in industrial fields.

BACKGROUND OF THE INVENTION

Superabsorbent refers to a water-swellable, water-insoluble, organic or inorganic material capable of absorbing at least about 10 times its weight and up to about 30 times its weight in an aqueous solution containing 0.9 weight percent sodium chloride solution in water. A superabsorbent polymer is a crosslinked polymer which is capable of absorbing large amounts of aqueous liquids and body fluids, such as urine or blood, with swelling and the formation of hydrogels, and of retaining them under a certain pressure in accordance with the general definition of superabsorbent.

The superabsorbent polymers that are currently commercially available are crosslinked polyacrylic acids or crosslinked starch-acrylic acid graft polymers, in which some of the carboxyl groups are neutralized with sodium hydroxide solution or potassium hydroxide solution. As a result of these characteristic properties, these polymers are chiefly used for incorporation into sanitary articles, such as babies' diapers, incontinence products or sanitary towels.

For fit, comfort and aesthetic reasons and from environmental aspects, there is an increasing trend to make sanitary articles smaller and thinner. This is being accomplished by reducing the content of the high volume fluff fiber of these articles. To ensure a constant total retention capacity of body fluids in the sanitary articles, more superabsorbent polymer content is being used in these sanitary articles. As a result of this, superabsorbent polymers must have increased permeability characteristics while retaining other characteristics such as adequate absorption and retention.

Permeability is a measure of the effective connectedness of a porous structure, be it a mat of fiber of a slab of foam or, in this case, crosslinked polymers and may be specified in terms of the void fraction and extent of connectedness of the superabsorbent polymer. Gel permeability is a property of the mass of particles as a whole and is related to particle size distribution, particle shape, the connectedness of the open pores, shear modulus and surface modification of the swollen gel. In practical terms, the permeability of the superabsorbent polymer is a measure of how rapidly liquid flows through the mass of swollen particles. Low permeability indicates that liquid cannot flow readily through the superabsorbent polymer, which is generally referred to gel blocking, and that any forced flow of liquid (such as a second application of urine during use of the diaper) must take an alternate path (e.g., diaper leakage).

In particular, gel blocking is a well-known problem that may be associated with the use of superabsorbent polymers in absorbent articles such as diapers. Gel blocking occurs when rapid expansion of the superabsorbent polymer particles around the point of entry of body fluid into an absorbent article causes a closing of the interstitial spaces and pores in the SAP-fluff matrix. Since the transport of liquid by diffusion through swollen hydrogel is much slower than transport through the interstitial spaces, a sealing effect occurs in the area of fluid entry. This effect is referred to as gel blocking.

Transportation of liquid through swollen superabsorbent polymer particles themselves follows the laws of diffusion and is a very slow process which plays no role in the distribution of the liquid in the use situation of the sanitary article. In superabsorbent polymers, which cannot maintain an open bed structure to effect capillary transportation because of a lack of gel stability, the separation of the particles from one another has been ensured by embedding the superabsorbent polymer into a fiber matrix.

In diaper constructions, for what is called the next generation, there is less fiber material, or potentially none at all, in the absorber layer to assist in transportation of the liquid or maintenance of an open, fluid permeable structure. The superabsorbent polymer of these next generation diaper constructions must have a sufficiently high stability in the swollen state, generally called gel strength, so the swollen gel has a sufficient amount of capillary spaces through which liquid can be transported.

To obtain a superabsorbent polymer with high gel strength, the degree of crosslinking of the polymer may be increased, which necessarily results in a reduction in the swellability and the retention capacity. To achieve the increased permeabilities needed in extremely thin, next generation articles with low fiber content, current art has taught to increase the amount of crosslinking to have higher gel strength achieved, typically having a shear modulus of greater than 9,500 dynes/cm². However the absorption and retention values of the superabsorbent polymers are reduced to undesirably low levels. It is an important goal of the art of making superabsorbent polymers to develop a polymer having a high absorption and retention capacity for liquid in the after-surface crosslinking stage and increased permeability properties. It has been found that by using new surface modifications to the SAP particles, results of higher permeabilities without very high gel strengths and the undesirable associated low absorption values are achieved.

It is therefore an object of the present invention to provide an absorbing polymer composition that exhibits excellent properties such as capabilities of maintaining high liquid permeability and liquid retention even when the superabsorbent polymer is increased in percent by weight based on the absorbent structure.

SUMMARY OF THE INVENTION

The present invention is directed to a superabsorbent polymer having a gel bed permeability numeric value (GBP) is at least about $[54000e^{-0.18x}+75] \times 10^{-9}$ cm² where x is the numeric value of centrifuge retention capacity; and a shear modulus G' is less than about 9,500 dynes/cm².

The present invention is also directed to a superabsorbent polymer comprising from about 55 to about 99.9 wt. % of polymerizable unsaturated acid group containing monomers; from about 0.001 to about 5.0 wt. % of internal crosslinking agent; from about 0.001 to about 5.0 wt. % of surface crosslinking agent applied to the particle surface; from 0 to about 5 wt. % of a penetration modifier immediately before, during or immediately after the surface crosslinking step; from 0 to about 5 wt. % of a multivalent metal salt on the surface; from about 0 to 2 wt % surfactant on the surface; and from about 0.01 to about 5 wt % of an insoluble, inorganic powder wherein the composition has a degree of neutralization of more than about 25%; and a gel bed permeability numeric value (GBP) is at least about $[54000e^{-0.18x}+75] \times 10^{-9}$ cm$^2$ where x is the numeric value of centrifuge retention capacity; a shear modulus G' is less than about 9,500 dynes/cm$^2$ and an absorption against pressure of less than about 23 g/g.

The present invention is further directed to a superabsorbent polymer comprising from about 55 to about 99.9 wt. % of polymerizable unsaturated acid group containing monomers; from about 0.001 to about 5.0 wt. % of internal crosslinking agent; from about 0.001 to about 5.0 wt. % of surface crosslinking agent applied to the particle surface; from 0 to about 5 wt. % of a penetration modifier immediately before, during or immediately after the surface crosslinking step; from 0 to about 5 wt. % of a multivalent metal salt on the surface; from about 0 to 2 wt % surfactant on the surface and from about 0.01 to about 5 wt % of an insoluble, inorganic powder wherein the composition has a degree of neutralization of more than about 25%; and a gel bed permeability is at least $300 \times 10^{-9}$ cm$^2$ and greater than $[0.34(G')-2080] \times 10^{-9}$ cm$^2$ where G' is the numeric value of shear modulus in dynes/cm$^2$; and an absorption against pressure less than about 23 g/g.

In addition, the present invention includes a superabsorbent polymer including from about 55 to about 99.9 wt. % of polymerizable unsaturated acid group containing monomers; from about 0.001 to about 5.0 wt. % of internal crosslinking agent; from about 0.001 to about 5.0 wt. % of surface crosslinking agent applied to the particle surface; from 0 to about 5 wt. % of a penetration modifier immediately before, during or immediately after the surface crosslinking step; from 0 to about 5 wt. % of a multivalent metal salt on the surface; from about 0 to 2 wt % surfactant on the surface; and from about 0.01 to about 5 wt % of an insoluble, inorganic powder wherein the superabsorbent polymer has the characteristics of centrifuge retention capacity from about 27 to about 30 g/g; a shear modulus from about 6400 to 8000 dynes/cm$^2$ and a gel bed permeability from about 800 to about $1500 \times 10^{-9}$ cm$^2$ and having an absorption against pressure of less than about 23 g/g.

In addition the present invention is directed to absorbent compositions or sanitary articles that may contain superabsorbent polymers of the present invention.

DETAILED DESCRIPTION OF THE INVENTION

Figure 1:
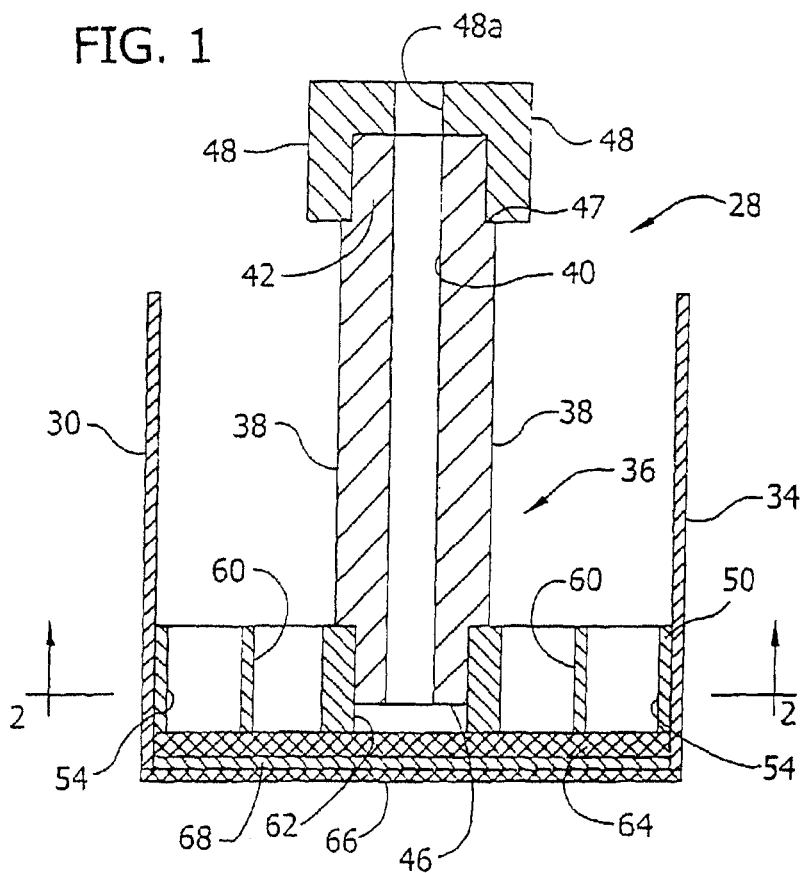
FIG. 1 is a cross-section of apparatus for conducting a Permeability Test.

A suitable superabsorbent polymer may be selected from natural, biodegradable, synthetic and modified natural polymers and materials. The term crosslinked used in reference to the superabsorbent polymer refers to any means for effectively rendering normally water-soluble materials substantially water-insoluble but swellable. Such a crosslinking means can include for example, physical entanglement, crystalline domains, covalent bonds, ionic complexes and associations, hydrophilic associations such as hydrogen bonding, hydrophobic associations or Van der Waals forces. Superabsorbent polymers include internal crosslinking and surface crosslinking.

In one embodiment of the present invention, the superabsorbent polymer is a crosslinked polymer wherein the superabsorbent polymer has a gel bed permeability (GBP) numeric value of at least about $[54000e^{-0.18x}+75] \times 10^{-9}$ cm$^2$ where x is the numeric value of centrifuge retention capacity (CRC); and a shear modulus (G') of less than about 9,500 dynes/cm$^2$. Preferably, such superabsorbent polymers exhibit a centrifuge retention capacity from about 25 to 35 g/g, a shear modulus from 5000 to 8500 dynes/cm$^2$, and a gel bed permeability from about 500 to $2500 \times 10^{-9}$ cm$^2$, and an absorption against pressure of less than 23 g/g. One preferred embodiment is a such superabsorbent polymer having a centrifuge retention capacity from about 27 to about 30 g/g; a shear modulus from about 6400 to about 8000 dynes/cm$^2$; and a gel bed permeability from about 800 to about $1500 \times 10^{-9}$ cm$^2$ and an absorption against pressure of less than about 23 g/g. Other embodiments include, but not limited to, include a superabsorbent polymer according to the present invention wherein GBP is at least about $[54000e^{-0.175x}+100] \times 10^{-9}$ cm$^2$; or the GBP is at least about $[54000e^{-0.17x}+100] \times 10^{-9}$ cm$^2$; or wherein GBP is at least about $[54000e^{-0.165x}+100] \times 10^{-9}$ cm$^2$; or wherein the gel bed permeability is at least about $500 \times 10^{-9}$ cm$^2$; or the superabsorbent polymer having centrifuge retention capacity from about 27 to about 30 g/g; a shear modulus from about 6400 to 8000 dynes/cm$^2$, and a gel bed permeability from about $800 \times 10^{-9}$ cm$^2$ to about $1500 \times 10^{-9}$ cm$^2$; or a superabsorbent polymer according to the present invention having the characteristics of centrifuge retention capacity of at least about 30 g/g; a shear modulus from about 4500 to 6400 dynes/cm$^2$, and a gel bed permeability of at least about $600 \times 10^{-9}$ cm$^2$.

In one embodiment of the present invention, the superabsorbent polymer is a crosslinked polymer comprising a) from about 55 to about 99.9 wt. % of polymerizable unsaturated acid group containing monomers; b) from about 0.001 to about 5.0 wt. % of internal crosslinking agent; c) from about 0.001 to about 5.0 wt. % of surface crosslinking agent applied to the particle surface; d) from 0 to about 5 wt. % of a penetration modifier applied to the surface of the particle immediately before, during or immediately after the surface crosslinking step; e) from 0 to about 5 wt. % of a multivalent metal salt on the surface; and f) from about 0.01 to about 5 wt % of an insoluble, inorganic powder, and g) from about 0 to about 2% surface active agent on the surface, wherein the superabsorbent polymer has a degree of neutralization of more than about 25%; a gel bed permeability (GBP) numeric value of at least about $[54000e^{-0.18x}+75] \times 10^{-9}$ cm$^2$ where x is the numeric value of centrifuge retention capacity (CRC); a shear modulus (G') of less than about 9,500 dynes/cm$^2$ and an absorption against pressure (AAP) of less than about 23 g/g. Preferably, such superabsorbent polymers exhibit a centrifuge retention capacity from about 25 to 35 g/g, a shear modulus from 5000 to 8500 dynes/cm$^2$, and a gel bed permeability from about 500 to $2500 \times 10^{-9}$ cm$^2$, and an absorption against pressure of less than 23 g/g. One preferred embodiment is such a superabsorbent polymer having a centrifuge retention capacity from about 27 to about 30 g/g; a shear modulus from about 6400 to about 8,000 dynes/cm$^2$; and a gel bed permeability from about 800 to about 1500×10$^{-9}$ cm$^2$ and an absorption against pressure of less than about 23 g/g.

The superabsorbent polymer of the present invention is obtained by the initial polymerization of from about 55 to about 99.9 wt. % of polymerizable unsaturated acid group containing monomers. Suitable monomers include those containing carboxyl groups, such as acrylic acid, methacrylic acid or 2-acrylamido-2-methylpropanesulfonic acid, or mixtures of these monomers are preferred here. It is preferable for at least about 50-weight. %, and more preferably at least about 75 wt. % of the acid groups to be carboxyl groups. The acid groups are neutralized to the extent of at least about 25 mol %, that is, the acid groups are preferably present as sodium, potassium or ammonium salts. The degree of neutralization is preferably at least about 50 mol %. It is preferred to obtain polymers obtained by polymerization of acrylic acid or methacrylic acid, the carboxyl groups of which are neutralized to the extent of 50-80 mol %, in the presence of internal crosslinking agents.

Further monomers, which can be used for the preparation of the absorbent polymers according to the invention, are 0-40 wt. % of ethylenically unsaturated monomers which can be copolymerized with a), such as e.g. acrylamide, methacrylamide, hydroxyethyl acrylate, dimethylaminoalkyl(meth)-acrylate, ethoxylated (meth)-acrylates, dimethylaminopropylacrylamide or acrylamidopropyltrimethylammonium chloride. More than 40 wt. % of these monomers can impair the swellability of the polymers.

The internal crosslinking agent has at least two ethylenically unsaturated double bonds or one ethylenically unsaturated double bond and one functional group which is reactive towards acid groups of the polymerizable unsaturated acid group containing monomers or several functional groups which are reactive towards acid groups can be used as the internal crosslinking component and which is present during the polymerization of the polymerizable unsaturated acid group containing monomers.

Examples of internal crosslinking agents include aliphatic unsaturated amides, such as methylenebisacryl- or -methacrylamide or ethylenebisacrylamide, and furthermore aliphatic esters of polyols or alkoxylated polyols with ethylenically unsaturated acids, such as di(meth)acrylates or tri(meth)acrylates of butanediol or ethylene glycol, polyglycols or trimethylolpropane, di- and triacrylate esters of trimethylolpropane which is preferably oxyalkylated, preferably ethoxylated, with 1 to 30 mol of alkylene oxide, acrylate and methacrylate esters of glycerol and pentaerythritol and of glycerol and pentaerythritol oxyethylated with preferably 1 to 30 mol of ethylene oxide and furthermore allyl compounds, such as allyl(meth)acrylate, alkoxylated allyl(meth)acrylate reacted with preferably 1 to 30 mol of ethylene oxide, triallyl cyanurate, triallyl isocyanurate, maleic acid diallyl ester, poly-allyl esters, tetraallyloxyethane, triallyamine, tetraallylethylenediamine, diols, polyols, hydroxy allyl or acrylate compounds and allyl esters of phosphoric acid or phosphorous acid, and furthermore monomers which are capable of crosslinking, such as N-methylol compounds of unsaturated amides, such as of methacrylamide or acrylamide, and the ethers derived there from. Ionic crosslinkers such as multivalent metal salts may also be employed. Mixtures of the crosslinking agents mentioned can also be employed. The content of the internal crosslinking agents is from about 0.01 to about 5 wt. %, and preferably from about 0.1 to about 3.0 wt. %, based on the total amount of the polymerizable unsaturated acid group containing monomers.

The usual initiators, such as e.g. azo or peroxo compounds, redox systems or UV initiators, (sensitizers), and/or radiation are used for initiation of the free-radical polymerization.

The absorbent polymers are surface crosslinked after polymerization. Surface crosslinking is any process that increases the crosslink density of the polymer matrix in the vicinity of the superabsorbent particle surface with respect to the crosslinking density of the particle interior. The absorbent polymers are typically surface crosslinked by the addition of a surface crosslinking agent. Preferred surface crosslinking agents include chemicals with one or more functional groups, which are reactive towards pendant groups of the polymer chains, typically the acid groups. The content of the surface crosslinking agents is from about 0.01 to about 5 wt. %, and preferably from about 0.1 to about 3.0 wt. %, based on the weight of the dry polymer. A heating step is preferred after addition of the surface crosslinking agent.

Generally the present invention includes coating the particulate superabsorbent polymer with an alkylene carbonate followed by heating to effect surface crosslinking to improve the surface crosslinking density and the gel strength characteristics. More specifically a surface crosslinking agent is coated onto the particulate by mixing the polymer with an aqueous alcoholic solution of the alkylene carbonate surface cross linking agent. The amount of alcohol is determined by the solubility of the alkylene carbonate and is kept as low as possible for technical reasons, for instance protection against explosions. Suitable alcohols are methanol, ethanol, butanol, or butyl glycol as well as mixtures of these alcohols. The preferred solvent is water, which typically is used in an amount of 0.3 to 5.0% by weight, relative to particulate superabsorbent polymer. In some instances, the alkylene carbonate surface cross linking agent is dissolved in water, without any alcohol. It is also possible to apply the alkylene carbonate surface cross linking agent from a powder mixture, for example, with an inorganic carrier material, such as SiO$_2$, or in the vapor state by sublimation of the alkylene carbonate.

To achieve the desired surface cross linking properties, the alkylene carbonate has to be distributed evenly on the particulate superabsorbent polymer. For this purpose, mixing is effected in suitable mixers, such as fluidized bed mixers, paddle mixers, milling rolls, or twin-worm mixers. It is also possible to carry out the coating of the particular superabsorbent polymer during one of the process steps in the production of the particulate superabsorbent polymer. A particularly suitable process for this purpose is the inverse suspension polymerization process.

The thermal treatment, which follows the coating treatment, is carried out as follows. In general, the thermal treatment is at a temperature between 100 and 300° C. However, if the preferred alkylene carbonates are used, then the thermal treatment is at a temperature between 150 and 250° C. The treatment temperature depends on the dwell time and the kind of alkylene carbonate. At a temperature of 150° C., the thermal treatment is carried out for one hour or longer. On the other hand, at a temperature of 250° C., a few minutes, e.g., 0.5 to 5 minutes, are sufficient to achieve the desired surface cross linking properties. The thermal treatment may be carried out in conventional dryers or ovens.

While particles are the used by way of example of the physical form of superabsorbent polymers, the invention is not limited to this form and is applicable to other forms such as fibers, foams, films, beads, rods and the like.

The absorbent polymers according to the invention can comprise include from 0 to about 5 wt % of a penetration modifier that is added immediately before, during or immediately after the surface crosslinking agent. Examples of penetration modifiers include compounds which alter the penetration depth of surface-modifying agents into the superabsorbent polymer particle, fiber, film, foam or bead by changing the viscosity, surface tension, ionic character or adhesion of said agents or medium in which these agents are applied. Preferred penetration modifiers are, polyethylene glycols, tetraethylene glycol dimethyl ether, monovalent metal salts, surfactants and water soluble polymers.

The absorbent polymers according to the invention can comprise include from 0 to about 5 wt % of a multivalent metal salt, based on the weight of the mixture, on the surface of the polymer. The multivalent metal salt is preferably water soluble. Examples of preferred metal cations include the cations of Al, Fe, Zr, Mg and Zn. Preferably, the metal cation has a valence of at least +3, with Al being most preferred. Examples of preferred anions in the multivalent metal salt include halides, chlorohydrates, sulfates, nitrates and acetates, with chlorides, sulfates, chlorohydrates and acetates being preferred, chlorohydrates and sulfates being more preferred and sulfates being the most preferred. Aluminium sulfate is the most preferred multivalent metal salt and is readily commercially available. The preferred form of aluminum sulfate is hydrated aluminum sulfate, preferably aluminum sulfate having from 12 to 14 waters of hydration. Mixtures of multivalent metal salts can be employed.

The polymer and multivalent metal salt suitably are mixed by dry blending, or preferably in solution, using means well known to those skilled in the art. Aqueous solutions are preferred. With dry blending, a binder may be employed in an amount which is sufficient to ensure that a substantially uniform mixture of the salt and the superabsorbent polymer is maintained. The binder may be water or a nonvolatile organic compound having a boiling point of at least 150° C. Examples of binders include water, polyols such as propylene glycol, glycerin and poly(ethylene glycol).

The absorbent polymers according to the invention can comprise include from about 0.01 to about 5 wt % of water-insoluble, inorganic powder. Examples of insoluble, inorganic powders include silicon dioxide, silicic acid, silicates, titanium dioxide, aluminium oxide, magnesium oxide, zinc oxide, talc, calcium phosphate, clays, diatomaceous earth, zeolites, bentonite, kaolin, hydrotalcite, activated clays, etc. The insoluble inorganic powder additive may be a single compound or a mixture of compounds selected from the above list. Of all these examples, microscopic noncrystal silicon dioxide or aluminium oxide preferred. Further, a preferred particle diameter of the inorganic powder is 1,000 μm or smaller, and more preferably 100 μm or smaller. The superabsorbent polymer according to the invention may also include the addition of from 0 to about 5 wt % of a surfactant to the polymer particle surface. It is preferred that these be added immediately prior to, during or immediately after the surface crosslinking step.

Examples of such surfactants include anionic, non-ionic, cationic and amphoteric surface active agents, such as fatty acid salts, coco amines and amides and their salts, alkylsulfuric ester salts, alkylbenzene sulfonic acid salts, dialkyl sulfo-succinate, alkyl phosphate salt, and polyoxyethylene alkyl sulfate salt; polyoxyethylene alkyl ether, polyoxyethylene alkyl phenol ether, polyoxyethylene fatty acid ester, sorbitan fatty acid ester, polyoxy sorbitan fatty acid ester, polyoxyethylene alkylamine, fatty acid esters, and oxyethylene-oxypropylene block polymer; alkyl amine salts, quaternary ammonium salts; and lauryl dimethylamine oxide. However, it is not necessary to restrict the surfactant to those mentioned above. Such surfactants may be used individually, or in combination.

The superabsorbent polymers may also include from 0 to about 30 wt. % of water-soluble polymers, such as partly or completely hydrolysed polyvinyl acetate, polyvinylpyrrolidone, starch or starch derivatives, polyglycols or polyacrylic acids, preferably in polymerized-in form. The molecular weight of these polymers is not critical as long as they are water-soluble. Preferred water-soluble polymers are starch and polyvinyl alcohol. The preferred content of such water-soluble polymers in the absorbent polymer according to the invention is 0-30 wt. %, preferably 0-5 wt. %, based on the total amount of components a) to d). The water-soluble polymers, preferably synthetic polymers, such as polyvinyl alcohol, can also serve as a graft base for the monomers to be polymerized.

It is sometimes desirable to employ surface additives that perform several roles during surface modifications. For example, a single additive may be a surfactant, viscosity modifier and react to crosslink polymer chains.

The superabsorbent polymers may also include from 0 to about 2.0 wt % of dedusting agents, such as hydrophilic and hydrophobic dedusting agents such as those described in U.S. Pat. Nos. 6,090,875 and 5,994,440 may also be employed in the process of the invention.

Further additives of the superabsorbent polymers according to the invention may optionally be employed, such as odor-binding substances, such as cyclodextrins, zeolites, inorganic or organic salts and similar materials; anti-caking additives, flow modification agents and the like.

The polymers according to the invention are preferably prepared by two methods. The polymers can be prepared continuously or discontinuously in a large-scale industrial manner by the abovementioned known process, the after-crosslinking according to the invention being carried out accordingly.

According to the first method, the partly neutralized monomer, preferably acrylic acid, is converted into a gel by free-radical polymerization in aqueous solution in the presence of crosslinking agents and optionally further components, and the gel is comminuted, dried, ground and sieved off to the desired particle size. This solution polymerization can be carried out continuously or discontinuously.

Inverse suspension and emulsion polymerization can also be used for preparation of the products according to the invention. According to these processes, an aqueous, partly neutralized solution of monomers, preferably acrylic acid, is dispersed in a hydrophobic, organic solvent with the aid of protective colloids and/or emulsifiers and the polymerization is started by free radical initiators. The internal crosslinking agents either are dissolved in the monomer solution and are metered in together with this, or are added separately and optionally during the polymerization. The addition of a water-soluble polymer d) as the graft base optionally takes place via the monomer solution or by direct introduction into the oily phase. The water is then removed azeotropically from the mixture and the polymer is filtered off and optionally dried. Internal crosslinking can be carried out by polymerizing-in a polyfunctional crosslinking agent dissolved in the monomer solution and/or by reaction of suitable crosslinking agents with functional groups of the polymer during the polymerization steps.

In one embodiment, the superabsorbent polymer is used in the form of discrete particles. Superabsorbent polymer particles can be of any suitable shape, for example, spiral or semi-spiral, cubic, rod-like, polyhedral etc. Particle shapes having a large greatest dimension/smallest dimension ratio, like needles, flakes or fibers are also contemplated for use herein. Conglomerates of particles of superabsorbent polymers my also be used.

Several different superabsorbent polymers that differ, for example, in the rate of absorption, permeability, storage capacity, absorption under pressure, particle size distribution or chemical composition can be simultaneously used together.

The superabsorbent polymer of the present invention has certain characteristics, or properties, as measured by Gel Bed Permeability (GBP), Centrifuge Retention Capacity (CRC), Absorption Against Pressure (AAP) and Shear Modulus (G'). The Gel Bed Permeability Test (GBP), is a measurement of the permeability of a swollen bed of superabsorbent material in $cm^2$ (e.g., separate from the absorbent structure) under a confining pressure after what is commonly referred to as "free swell" conditions. The term "free swell" means that the superabsorbent material is allowed to swell without a swell restraining load upon absorbing test solution as will be described.

The Centrifuge Retention Capacity Test (CRC) measures the ability of the superabsorbent material to retain liquid therein after being saturated and subjected to centrifugation under controlled conditions. The resultant retention capacity is stated as grams of liquid retained per gram weight of the sample (g/g).

The Absorption Against Pressure Test (AAP) measures the ability of each sample of SAP to absorb fluid out of a reservoir while working under a pre-determined load or pressure, 0.7 psi in this case, and conducted at ambient conditions of temperature.

The Shear Modulus Test measures the gel strength or gel deformation tendency of the SAP. Shear modulus is measured, by a procedure that involves the use of a Rank Brothers Pulse Shearometer to measure the velocity of a torsional shear wave through the swollen gel. The SAP sample tested in this manner is swollen to its equilibrium gel volume with synthetic urine and the interparticulate or interstitial water removed. Using a procedure described in greater detail hereinafter in the Test Methods section, the shear modulus of the resulting SAP in dynes/$cm^2$ is then subsequently calculated from torsional shear wave velocity. This method avoids many of the problems associated with measuring the shear modulus of surface cross linked superabsorbent polymers using traditional constant stress and constant strain rheometers or rheometers that rely on measuring the phase angle shift between stress and strain.

Figure 4:
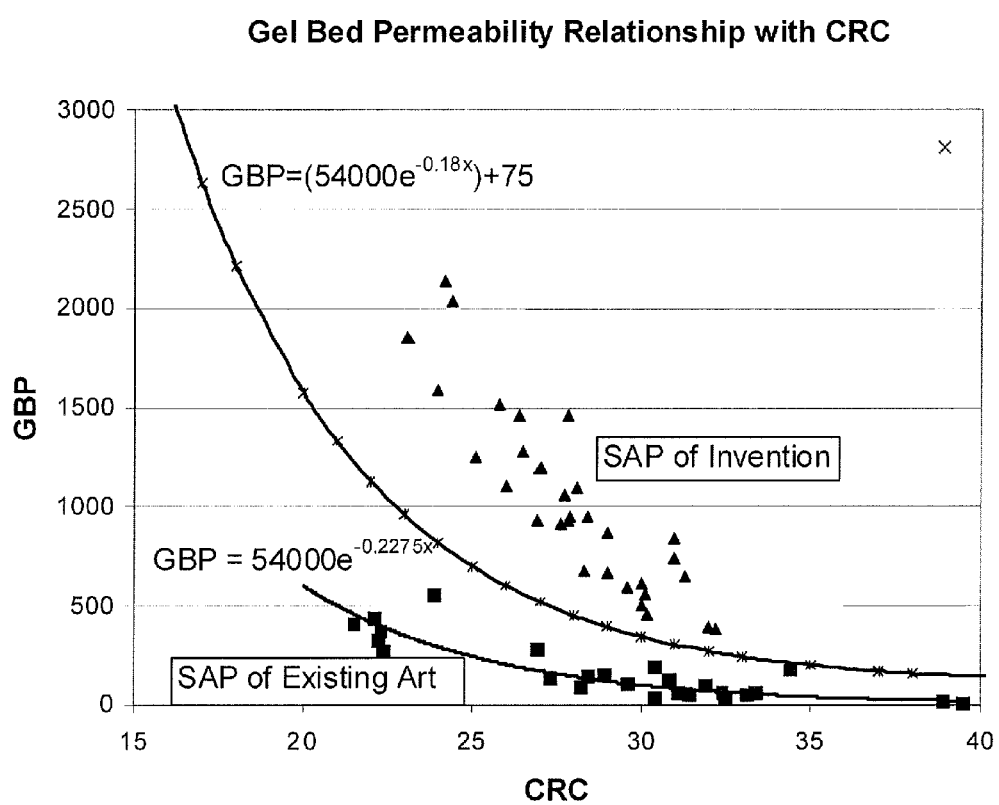
FIG. 4 is a graph depicting the relationship of Gel Bed Permeability and Centrifuge Retention Capacity.

As shown in FIG. 4, the drawing shows a relationship between gel bed permeability and centrifuge retention capacity. The products according to the invention with this outstanding combination of properties of very high GBP values, high CRC without an undesirably high shear modulus achieved by over crosslinking can be prepared without the use of toxicologically unacceptable substances.

The polymers according to the invention can be employed in many products including sanitary towels, diapers or in wound coverings, they have the property that they rapidly absorb large amounts of menstrual blood, urine or other body fluids. Since the agents according to the invention retain the absorbed liquids even under pressure and additionally are capable of distributing further liquid within the construction in the swollen state, they are more preferably employed in higher concentrations, in respect of the hydrophilic fiber material, such as e.g. fluff, than was hitherto possible. They are also suitable for use as a homogeneous superabsorber layer without fluff content within the diaper construction, as a result of which particularly thin diapers are possible. The polymers are furthermore suitable for use in hygiene articles (incontinence products) for adults.

The preparation of laminates in the broadest sense, and of extruded and coextruded, wet- and dry-bonded, as well as subsequently bonded, structures are possible as further preparation processes. A combination of these possible processes with one another is also possible.

The polymers according to the invention are also employed in absorbent articles that are suitable for further uses. In particular, the polymers of this invention can be used in absorbent compositions for absorbents for water or aqueous liquids, preferably in constructions for absorption of body fluids, in foamed and non-foamed sheet-like structures, in packaging materials, in constructions for plant growing, as soil improvement agents or as active compound carriers. For this, they are processed to a web by mixing with paper or fluff or synthetic fibers or by distributing the superabsorbent polymers between substrates of paper, fluff or non-woven textiles or by processing into carrier materials.

They are further suited for use in absorbent compositions such as wound dressings, packaging, agricultural absorbents, food trays and pads, and the like.

Surprisingly, the superabsorbent polymers according to the invention show a significant improvement in permeability, i.e. an improvement in the transportation of liquid in the swollen state, while maintaining high absorption and retention capacity.

Test Methods

Gel Bed Permeability

Figure 2:
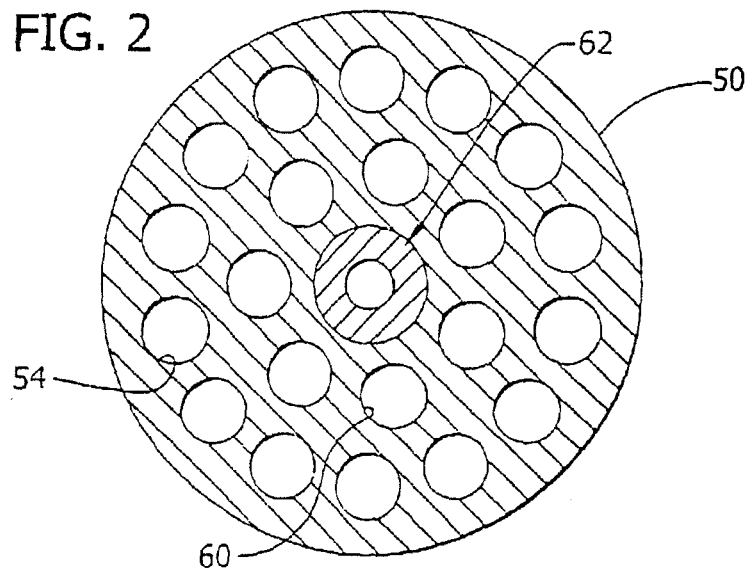
FIG. 2 is a section taken in the plane of line 2-2 of FIG. 1.

As used herein, the Gel Bed Permeability (GBP) Test determines the permeability of a swollen bed of superabsorbent polymer under what is commonly referred to as "free swell" conditions. The term "free swell" means that the superabsorbent polymer is allowed to swell without a swell restraining load upon absorbing test solution as will be described. A suitable apparatus for conducting a Permeability Test is shown in FIGS. 1 and 2 and indicated generally as 28. The test apparatus 28 comprises a sample container, generally indicated at 30, and a piston, generally indicated at 36. The piston 36 comprises a cylindrical LEXAN® shaft 38 having a concentric cylindrical hole 40 bored down the longitudinal axis of the shaft. Both ends of the shaft 38 are machined to provide upper and lower ends respectively designated 42, 46. A weight, indicated as 48, rests on one end 42 and has a cylindrical hole 48a bored through at least a portion of its center.

A circular piston head 50 is positioned on the other end 46 and is provided with a concentric inner ring of seven holes 60, each having a diameter of about 0.95 cm, and a concentric outer ring of fourteen holes 54, also each having a diameter of about 0.95 cm. The holes 54, 60 are bored from the top to the bottom of the piston head 50. The piston head 50 also has a cylindrical hole 62 bored in the center thereof to receive end 46 of the shaft 38. The bottom of the piston head 50 may also be covered with a biaxially stretched 400 mesh stainless steel screen 64.

The sample container 30 comprises a cylinder 34 and a 100 mesh stainless steel cloth screen 66 that is biaxially stretched to tautness and attached to the lower end of the cylinder. A superabsorbent polymer sample, indicated as 68 in FIG. 1, is supported on the screen 66 within the cylinder 34 during testing.

The cylinder 34 may be bored from a transparent LEXAN rod or equivalent material, or it may be cut from a LEXAN tubing or equivalent material, and has an inner diameter of about 6 cm (e.g., a cross sectional area of about 28.27 cm2), a wall thickness of about 0.5 cm and a height of approximately 5 cm. Drainage holes (not shown) are formed in the sidewall of the cylinder 34 at a height of approximately 4.0 cm above the screen 66 to allow liquid to drain from the cylinder to thereby maintain a fluid level in the sample container at approximately 4.0 cm above the screen 66. The piston head 50 is machined from a LEXAN rod or equivalent material and has a height of approximately 16 mm and a diameter sized such that it fits within the cylinder 34 with minimum wall clearance but still slides freely. The shaft 38 is machined from a LEXAN rod or equivalent material and has an outer diameter of about 2.22 cm and an inner diameter of about 0.64 cm.

The shaft upper end 42 is approximately 2.54 cm long and approximately 1.58 cm in diameter, forming an annular shoulder 47 to support the weight 48. The annular weight 48 has an inner diameter of about 1.59 cm so that it slips onto the upper end 42 of the shaft 38 and rests on the annular shoulder 47 formed thereon. The annular weight 48 can be made from stainless steel or from other suitable materials resistant to corrosion in the presence of the test solution, which is 0.9 weight percent sodium chloride solution in distilled water. The combined weight of the piston 36 and annular weight 48 equals approximately 596 grams (g), which corresponds to a pressure applied to the absorbent structure sample 68 of about 0.3 pounds per square inch (psi), or about 20.7 dynes/cm$^2$, over a sample area of about 28.27 cm$^2$.

When the test solution flows through the test apparatus during testing as described below, the sample container 30 generally rests on a 16 mesh rigid stainless steel support screen (not shown). Alternatively, the sample container 30 may rest on a support ring (not shown) diametrically sized substantially the same as the cylinder 34 so that the support ring does not restrict flow from the bottom of the container.

To conduct the Gel Bed Permeability Test under "free swell" conditions, the piston 36, with the weight 48 seated thereon, is placed in an empty sample container 30 and the height from the bottom of the weight 48 to the top of the cylinder 34 is measured using a caliper or suitable gauge accurate to 0.01 mm. It is important to measure the height of each sample container 30 empty and to keep track of which piston 36 and weight 48 is used when using multiple test apparatus. The same piston 36 and weight 48 should be used for measurement when the superabsorbent polymer sample 68 is later swollen following saturation.

The sample to be tested is prepared from superabsorbent material particles which are prescreened through a U.S. standard 30 mesh screen and retained on a U.S. standard 50 mesh screen. As a result, the test sample comprises particles sized in the range of about 300 to about 600 microns. The particles can be prescreened by hand or automatically. Approximately 0.9 grams of the sample is placed in the sample container 30, and the container, without the piston 36 and weight 48 therein, is then submerged in the test solution for a time period of about 60 minutes to saturate the sample and allow the sample to swell free of any restraining load.

At the end of this period, the piston 36 and weight 48 assembly is placed on the saturated sample 68 in the sample container 30 and then the sample container 30, piston 36, weight 48, and sample 68 are removed from the solution. The thickness of the saturated sample 68 is determined by again measuring the height from the bottom of the weight 48 to the top of the cylinder 34, using the same caliper or gauge used previously provided that the zero point is unchanged from the initial height measurement. The height measurement obtained from measuring the empty sample container 30, piston 36, and weight 48 is subtracted from the height measurement obtained after saturating the sample 68. The resulting value is the thickness, or height "H" of the swollen sample.

The permeability measurement is initiated by delivering a flow of the test solution into the sample container 30 with the saturated sample 68, piston 36, and weight 48 inside. The flow rate of test solution into the container is adjusted to maintain a fluid height of about 4.0 cm above the bottom of the sample container. The quantity of solution passing through the sample 68 versus time is measured gravimetrically. Data points are collected every second for at least twenty seconds once the fluid level has been stabilized to and maintained at about 4.0 cm in height. The flow rate Q through the swollen sample 68 is determined in units of grams/second (g/g) by a linear least-square fit of fluid passing through the sample 68 (in grams) versus time (in seconds).

Permeability in cm$^2$ is obtained by the following equation:

$$K=[Q*H*Mu]/[A*Rho*P]$$

where K=Permeability (cm$^2$), Q=flow rate (g/rate), H=height of sample (cm), Mu=liquid viscosity (poise) (approximately one centipoise for the test solution used with the Test), A=cross-sectional area for liquid flow (cm$^2$), Rho=liquid density (g/cm$^3$), for the test solution used with this Test) and P=hydrostatic pressure (dynes/cm$^2$) (normally approximately 3,923 dynes/cm$^2$). The hydrostatic pressure is calculated from $$P=Rho*g*h$$

where Rho=liquid density (g/cm$^3$), g=gravitational acceleration, nominally 981 cm/sec$^2$, and h=fluid height. e.g., 4.0 cm for the Permeability Test described herein.

A minimum of three samples are tested and the results are averaged to determine the gel bed permeability of the sample. The samples are tested at 23±1 degrees Celcius at 50±2 percent relative humidity.

Absorption Against Pressure (AAP)

The ability of a water-absorbing polymerizate to absorb liquid from a reservoir under a defined pressure (Absorption Against Pressure AAP (0.7 psi=49 g/cm$^2$)) is determined as follows: 900 mg of test substance is weighed in a plastic cylinder (inner diameter=6 cm, height=5 cm) having a screen fabric (mesh width=400 mesh) as bottom, dispersed uniformly, and weighted using a defined weight in the form of a plastic plate (diameter=5.98 cm), together with a metal piston (diameter=5.98 cm). The plastic plate is situated between the test substance and the metal piston. Thereafter, the entire testing unit is placed on a glass filter plate (diameter=12 cm, porosity=0) which is covered with a filter paper and soaked with 0.9% NaCl solution. The filter plate is embedded in the NaCl solution up to its top edge. The test substance is allowed to absorb liquid for 60 minutes.

The plastic spacer and then the stainless steel weight were carefully placed into the cylinder. The weight of the completed AAP apparatus was recorded (A). The stainless steel weight exerted a pressure load of about 49 g/cm$^2$. (It is noted 49 g/cm$^2$=0.7 psi.).

After the 1 hour, the apparatus with the swollen sample was re-weighed, and the weight recorded (B). The gram amount of the NaCl solution that had been retained per gram of sample was calculated according to the following equation:

$$AAP=(B-A)/E$$

where, AAP is in g/g at 0.7 psi. A is weight in g of AAP apparatus with sample prior to absorbing NaCl solution. B is weight in g of AAP apparatus with sample after absorbing the test solution for 1 hour and E is actual weight in g of sample.

Centrifuge Retention Capacity Test

The Centrifuge Retention Capacity (CRC) Test measures the ability of the superabsorbent polymer to retain liquid therein after being saturated and subjected to centrifugation under controlled conditions. The resultant retention capacity is stated as grams of liquid retained per gram weight of the sample (g/g). The sample to be tested is prepared from particles which is pre-screened through a U.S. standard 30 mesh screen and retained on a U.S. standard 50 mesh screen. As a result, the superabsorbent polymer sample comprises particles sized in the range of about 300 to about 600 microns. The particles can be pre-screened by hand or automatically.

The retention capacity is measured by placing about 0.2 grams of the pre-screened superabsorbent polymer sample into a water-permeable bag that will contain the sample while allowing a test solution (0.9 weight percent sodium chloride in distilled water) to be freely absorbed by the sample. A heat-sealable tea bag material, such as that available from Dexter Corporation of Windsor Locks, Conn., U.S.A., as model designation 1234T heat sealable filter paper works well for most applications. The bag is formed by folding a 5-inch by 3-inch sample of the bag material in half and heat-sealing two of the open edges to form a 2.5-inch by 3-inch rectangular pouch. The heat seals should be about 0.25 inches inside the edge of the material. After the sample is place in the pouch, the remaining open edge of the pouch is also heat-sealed. Empty bags are also made to serve as controls. Three samples are prepared for each superabsorbent polymer to be tested.

The sealed bags are placed submerged in a pan of the test solution at 23° C., making sure that the bags are held down until they are completely wetted. After wetting, the samples remain in the solution for about 30 minutes, at which time they are removed from the solution and temporarily laid on a non-absorbent flat surface.

The wet bags are then placed into the basket of a suitable centrifuge capable of subjecting the samples to a g-force of about 350. One suitable centrifuge is a Clay Adams Dynac II, model #0103, having a water collection basket, a digital rpm gauge, and a machined drainage basket adapted to hold and drain the flat bag samples. Where multiple samples are centrifuged, the samples must be placed in opposing positions within the centrifuge to balance the basket when spinning. The bags (including the wet, empty bags) are centrifuged at about 1,600 rpm (e.g., to achieve a target g-force of about 350), for 3 minutes. The bags are removed and weighed, with the empty bags (controls) being weighed first, followed by the bags containing the superabsorbent polymer samples. The amount of solution retained by the superabsorbent polymer sample, taking into account the solution retained by the bag itself, is the centrifuge retention capacity (CRC) of the superabsorbent polymer, expressed as grams of fluid per gram of superabsorbent polymer. More particularly, the retention capacity is determined as:

$$\frac{\text{sample/bag after centrifuge} - \text{empty bag after centrifuge} - \text{dry sample weight}}{\text{dry sample weight}}$$

The three samples are tested and the results are averaged to determine the retention capacity (CRC) of the superabsorbent polymer.

The superabsorbent polymer also suitably has a gel bed permeability (GBP) as determined by the Gel Bed Permeability Test described previously of at least $[54000e^{-0.18x}+75] \times 10^{-9}$ cm$^2$, where x is the numeric value of centrifuge retention capacity; preferably GBP is at least about $[54000e^{-0.175x}+100] \times 10^{-9}$ cm$^2$ and more preferably GBP is at least about $[54000e^{-0.17x}+100] \times 10^{-9}$ cm$^2$ and most preferably GBP is at least about $[54000e^{-0.165x}+100] \times 10^{-9}$ cm$^2$.

Gel Strength/Shear Modulus Test

Figure 3:
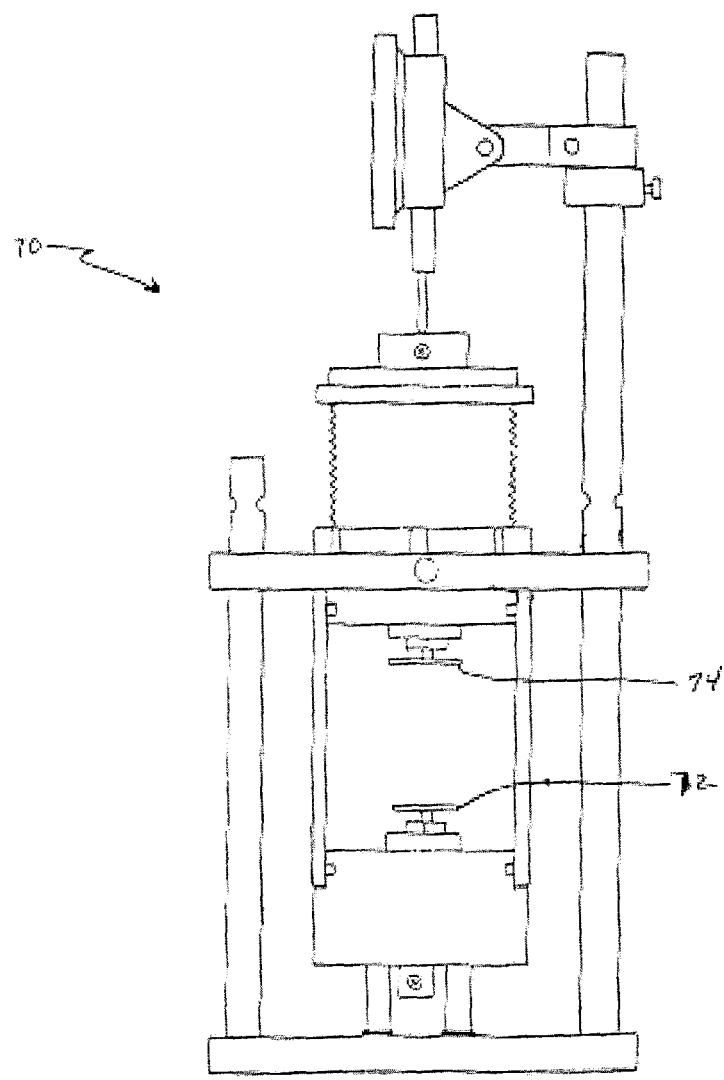
FIG. 3 is an elevation view of apparatus for conducting a Shear Modulus Test.

The Shear Modulus Test measures the gel strength, or gel deformation tendency, of the superabsorbent material. The shear modulus is measured using a Rank Brothers Pulse Shearometer, shown in FIG. 3 and generally referred to as 70, that comprises a circular lower plate, 72 onto which the swollen superabsorbent polymer is placed. For this case reference is made to the operating manual "The Simple Solution to Shear Modulus Measurements" for the Rank Pulse Shearometer™. The instrument is constructed in such a way that a torsional shear wave can be propagated between a pair of parallel disks 72 and 74. Each disc is mounted on a piezo-electric transducer: one being used to initiate the shear wave, the other to detect the arrival of this wave a short time later. The separation of the disks can be varied by means of a screw adjustment and then measured with a dial gauge. The propagation time of the shear wave is measured for each given disk separation. It is then possible to determine the wave velocity from the slope of a graph of propagation time plotted against disk separation. A value of shear modulus can then be calculated form the approximation:

$$G=\rho V^2$$

wherein G is the shear modulus in Nm$^{-2}$; $\rho$ is the density of the superabsorbent polymer sample in kg·m$^{-3}$ and V is the wave propagation velocity in ms$^{-1}$.

The sample being tested is swollen to its gel volume in a synthetic urine. Excess free synthetic urine is removed from the sample by blotting on two paper towels for exactly one minute, strain.

The shear modulus (G') of the superabsorbent sample is calculated from the following formula:

$$G'=\text{Density} \times (\text{shear wave velocity}) \times (\text{shear wave velocity}).$$

The elasticity of the material may be related to the velocity of the wave in the following manner: For a passage of a shear wave through the superabsorbent polymer, the storage component of the dynamic modulus (the elasticity), G', can be represented by the following equation:

$$G'=[V^2\rho(1-n^2)]/(1+n^2)^2$$

wherein V is the propagation velocity of light; $\rho$ is the density of the superabsorbent polymer; and n is the ratio of the wavelength to the critical damping length. Measurements of shear modulus can be obtained through consultancy groups such as the Bristol Colloid Center, University of Bristol, Bristol UK. In addition Rank Shearometers are offered on the Internet.

Preparation for performing the shear modulus test includes preparing synthetic urine which is made of 1% aqueous Triton X-100, 7.50 g; sodium chloride 30.00 g; anhydrous CaCl$_2$, 0.68 g; MgCl$_2$6H$_2$O 1.80 g; and DI water 3000.0 g.

About 90 g of synthetic urine are placed into 3 large beakers. Then about 3.00 g of SAP is placed into aluminium weighing pans. The SAP is added to a first beaker of stirring synthetic urine and begins timing. Each sample is allowed to swell to its equilibrium value, typically for 30 minutes. Each sample was stirred to ensure uniform fluid distribution. A large metal spatula was used to remove the hydrated superabsorbent polymer from the beakers and spread evenly on 2 Wipe Alls L20 Kimtowels®, available from Kimberly-Clark, which are folded in half and stacked. The superabsorbent polymer samples are blotted for exactly 60 seconds on the Wipe Alls. The spatula is used to spread the polymer out over the paper towelling, only lightly pressing the polymer onto the towel. No more force is applied than that required to distribute the polymer. The polymer is scraped up with the spatula and returned to the beaker after 60 seconds. The beaker is covered with foil or film until the sample is measured.

The shear moduli of the samples are measured within one hour of sample preparation. The sample is transferred to a shearometer tube and placed on the lower disk 72, filling the shearometer tube to a height of at least 18 mm above the lower disk. The top disk 74 assembly is lowered slowly until the top disk is exactly a distance of 12 mm from the bottom disk. The shear modulus G' is measured and recorded by measuring the time required for the torsional wave to pass through the SAP at plate distances of 12 mm to 6 mm, measured at 1 mm decreasing increments. The slope of the linear time to disk separation distance plot provides the shear wave velocity used to calculate the shear modulus, G'.

EXAMPLES

The following examples are provided to illustrate the invention, and do not limit the scope of the claims. Unless otherwise stated all parts and percentages are by weight.

Example 1

In an insulated, flat-bottomed reaction vessel, 800 g of acrylic acid was added to 3090.26 g of distilled water and the solution cooled to 25° C. A second solution of 1600 g of acrylic acid containing 4.8 g of triallyamine, 120.53 g 50 wt % methoxypolyethyleneglycol(750)monomethacrylate in acrylic acid and 3.6 g of trimethylolpropanetriacrylate with 9 moles of ethoxylation were then added to the first solution, followed by cooling to 15° C., the addition of 24.0 g of allyl ether acrylate with 10 moles of ethoxylation, and additional cooling to 5° C., all while stirring. The monomer solution was then polymerized with a mixture of 150 ppm hydrogen peroxide, 200 ppm azo-bis-(2-amidino-propene)dihydrochloride, 350 ppm sodiumpersulfate and 100 ppm sodium erythorbate under adiabatic conditions and held near $T_{max}$ for 25 minutes. The resulting gel was chopped and extruded with a Hobarth 4M6 commercial extruder, followed by drying in a Procter & Schwartz Model 062 forced air oven at 175° C. for 10 minutes with upflow and 6 minutes with downflow air on a 20 in×40 in perforated metal tray to a final product moisture level of less than 5 wt %. The dried material was coarse ground in a Prodeva Model 315-S crusher, milled in an MPI 666-F three stage roller mill and sieved with an Minox MTS 600DS3V to remove particles greater than 850 microns and smaller than 150 microns. 400 g of the sieved powder was then blended uniformly with 0.5 wt % Aerosil 200 fumed silica and 0.2 wt % aluminium sulfate, followed by the uniform spray application of a solution 0.1 wt % disodium cocoamphopropionate, 0.5 wt % tetraethyleneglycol dimethylether, and 1.0 wt % ethylene carbonate in 4 g of water, using a finely atomized spray from a Paasche VL sprayer while the SAP particles are fluidized in air and continuously mixed. All wt % values based on the weight of dry SAP powder. The coated material was then heated for 20 minutes at 180° C. in a General Signal/BM Model OV-510A-3 forced air oven.

Example 2

Same as Example 1 except the sample was heated for 30 minutes at 180° C.

Example 3

Same as Example 1 except the sample was heated for 40 minutes at 180° C.

Example 4

In an insulated, flat-bottomed reaction vessel, 800 g of acrylic acid was added to 3090.26 g of distilled water and the solution cooled to 25° C. A second solution of 1600 g of acrylic acid containing 9.6 g of triallyamine, 120.53 g 50 wt % methoxypolyethyleneglycol(750)monomethacrylate in acrylic acid and 7.2 g of trimethylolpropanetriacrylate with 9 moles of ethoxylation were then added to the first solution, followed by cooling to 15° C., the addition of 24.0 g of allyl ether acrylate with 10 moles of ethoxylation, and additional cooling to 5° C., all while stirring. The monomer solution was then polymerized with a mixture of 150 ppm hydrogen peroxide, 200 ppm azo-bis-(2-amidino-propene)dihydrochloride, 350 ppm sodiumpersulfate and 100 ppm sodium erythorbate under adiabatic conditions and held near $T_{max}$ for 25 minutes. The resulting gel was chopped and extruded with a Hobarth 4M6 commercial extruder, followed by drying in a Procter & Schwartz Model 062 forced air oven at 175° C. for 10 minutes with upflow and 6 minutes with downflow air on a 20 in×40 in perforated metal tray to a final product moisture level of less than 5 wt %. The dried material was coarse ground in a Prodeva Model 315-S crusher, milled in an MPI 666-F three stage roller mill and sieved with an Minox MTS 600DS3V to remove particles greater than 850 microns and smaller than 150 microns. 400 g of the sieved powder was then blended uniformly with 0.5 wt % Aerosil 200 fumed silica and 0.2 wt % aluminium sulfate, followed by the uniform spray application of a solution 0.1 wt % disodium cocoamphopropionate, 0.5 wt % tetraethyleneglycol dimethylether, and 1.0 wt % ethylene carbonate in 4 g of water, using a finely atomized spray from a Paasche VL sprayer while the SAP particles are fluidized in air and continuously mixed. All wt % values based on the weight of dry SAP powder. The coated material was then heated for 20 minutes at 180° C. in a General Signal/BM Model OV-510A-3 forced air oven.

Example 5

Same as example 4 except the sample was heated for 30 minutes at 180° C.

Example 6

Same as example 4 except the sample was heated for 40 minutes at 180° C.

Example 7

In an insulated, flat-bottomed reaction vessel, 800 g of acrylic acid was added to 3090.26 g of distilled water and the solution cooled to 25° C. A second solution of 1600 g of acrylic acid containing 4.2 g of triallyamine, 120.53 g of 50 wt % methoxypolyethyleneglycol(750)monomethacrylate in acrylic acid and 2.4 g of trimethylolpropanetriacrylate with 9 moles of ethoxylation were then added to the first solution, followed by cooling to 15° C., the addition of 24.0 g of allyl ether acrylate with 10 moles of ethoxylation, and additional cooling to 5° C., all while stirring. The monomer solution was then polymerized with a mixture of 150 ppm hydrogen peroxide, 200 ppm azo-bis-(2-amidino-propene)dihydrochloride, 350 ppm sodiumpersulfate and 100 ppm sodium erythorbate under adiabatic conditions and held near $T_{max}$ for 25 minutes. The resulting gel was chopped and extruded with a Hobarth 4M6 commercial extruder, followed by drying in a Procter & Schwartz Model 062 forced air oven at 175° C. for 10 minutes with upflow and 6 minutes with downflow air on a 20 in×40 in perforated metal tray to a final product moisture level of less than 5 wt %. The dried material was coarse ground in a Prodeva Model 315-S crusher, milled in an MPI 666-F three stage roller mill and sieved with an Minox MTS 600DS3V to remove particles greater than 850 microns and smaller than 150 microns. 400 g of the sieved powder was then blended uniformly with 0.5 wt % Aerosil 200 fumed silica, followed by the uniform spray application of a solution containing 0.2 wt % aluminium sulfate, 0.1 wt % disodium cocoamphopropionate, 0.5 wt % tetraethyleneglycoldimethyether, and 1.0 wt % ethylene carbonate in 10 g of water, using a finely atomized spray from a Paasche VL sprayer while the SAP particles are fluidized in air. All wt % values based on the weight of dry SAP powder. The coated material was then heated for 20 minutes at 180° C. in a General Signal/BM Model OV-510A-3 forced air oven.

Example 8

Same as Example 7 except that the sample was heated for 40 minutes at 180° C.

Example 9

Same as Example 7 except that the sample was heated for 30 minutes at 180° C.

Example 10

In an insulated, flat-bottomed reaction vessel, 1866.7 g of 50% NaOH was added to 3090.26 g of distilled water and cooled to 25° C. 800 g of acrylic acid was then added to caustic solution and the solution again cooled to 25° C. A second solution of 1600 g of acrylic acid containing 4.8 g of triallyamine, 120.53 g of 50 wt % methoxypolyethyleneglycol(750)monomethacrylate in acrylic acid and 3.6 g of trimethylolpropanetriacrylate with 9 moles of ethoxylation were then added to the first solution, followed by cooling to 15° C., the addition of 24.0 g of hydroxymonoallyl ether with 10 moles of ethoxylation, and additional cooling to 5° C., all while stirring. The monomer solution was then polymerized with a mixture of 150 ppm hydrogen peroxide, 200 ppm azo-bis-(2-amidino-propene)dihydrochloride, 350 ppm sodiumpersulfate and 100 ppm sodium erythorbate (all as aqueous solutions) under adiabatic conditions and held near $T_{max}$ for 25 minutes. The resulting gel was chopped and extruded with a Hobarth 4M6 commercial extruder, followed by drying in a Procter & Schwartz Model 062 forced air oven at 175° C. for 10 minutes with upflow and 6 minutes with downflow air on a 20 in×40 in perforated metal tray to a final product moisture level of less than 5 wt %. The dried material was coarse ground in a Prodeva Model 315-S crusher, milled in an MPI 666-F three stage roller mill and sieved with an Minox MTS 600DS3V to remove particles greater than 850 microns and smaller than 150 microns. 400 g of the sieved powder was then blended uniformly with 0.5 wt % fumed alumina (Degussa Aluminaoxide C), followed by the uniform spray application of a solution containing 0.2 wt % sodium sulfate, 0.1 wt % cocomonoethanol amide with 4.5 moles ethoxylation, 0.5 wt % polyethylene glycol MW 600, and 0.5 wt % ethylene carbonate in 5 g of water, using a finely atomized spray while the SAP particles are fluidized in air. The coated material was then heated for 20 minutes at 180° C. in a General Signal/BM Model OV-510A-3 forced air oven.

Example 11

Similar to Example 10 except the sample was heated for 30 minutes at 180° C.

Example 12

Similar to Example 10 except the sample was heated for 40 minutes at 180° C.

Example 13

In an insulated, flat-bottomed reaction vessel, 1866.7 g of 50% NaOH was added to 3090.26 g of distilled water and cooled to 25° C. 800 g of acrylic acid was then added to caustic solution and the solution again cooled to 25° C. A second solution of 1600 g of acrylic acid containing 4.8 g of triallyamine, 120.53 g of 50 wt % methoxypolyethyleneglycol(750)monomethacrylate in acrylic acid and 3.6 g of trimethylolpropanetriacrylate with 9 moles of ethoxylation were then added to the first solution, followed by cooling to 15° C., the addition of 24.0 g of hydroxymonoallyl ether with 10 moles of ethoxylation, and additional cooling to 5° C., all while stirring. The monomer solution was then polymerized with a mixture of 150 ppm hydrogen peroxide, 200 ppm azo-bis-(2-amidino-propene)dihydrochloride, 350 ppm sodiumpersulfate and then 100 ppm sodium erythorbate (all aqueous solutions) under adiabatic conditions and held near $T_{max}$ for 25 minutes. The resulting gel was chopped and extruded with a Hobarth 4M6 commercial extruder, followed by drying in a Procter & Schwartz Model 062 forced air oven at 175° C. for 10 minutes with upflow and 6 minutes with downflow air on a 20 in×40 in perforated metal tray to a final product moisture level of less than 5 wt %. The dried material was coarse ground in a Prodeva Model 315-S crusher, milled in an MPI 666-F three stage roller mill and sieved with an Minox MTS 600DS3V to remove particles greater than 850 microns and smaller than 150 microns. 400 g of the sieved powder was then blended uniformly with 0.5 wt % fumed alumina (Degussa Aluminumaoxid C), followed by the uniform spray application of a solution containing 0.3 wt % aluminum sulfate, 0.1 wt % cocomonoethanol amide with 4.5 moles ethoxylation, 0.2 wt % polyethylene glycol MW 600, and 0.5 wt % ethylene carbonate in 5 g of water, using a finely atomized spray while the SAP particles are fluidized in air. The coated material was then heated for 20 minutes at 180° C. in a General Signal/BM Model OV-510A-3 forced air oven.

Example 14

Similar to Example 13 except the sample was heated for 30 minutes at 180° C.

Example 15

Similar to Example 13 except the sample was heated for 40 minutes at 180° C.

Example 16

In an insulated, flat-bottomed reaction vessel, 1866.7 g of 50% NaOH was added to 3090.26 g of distilled water and cooled to 25° C. 800 g of acrylic acid was then added to caustic solution and the solution again cooled to 25° C. A second solution of 1600 g of acrylic acid containing 4.8 g of triallyamine, 120.53 g of 50 wt % methoxypolyethyleneglycol(750)monomethacrylate in acrylic acid and 3.6 g of trimethylolpropanetriacrylate with 9 moles of ethoxylation were then added to the first solution, followed by cooling to 15° C., the addition of 24.0 g of hydroxymonoallyl ether with 10 moles of ethoxylation, and additional cooling to 5° C., all while stirring. The monomer solution was then polymerized with a mixture of 150 ppm hydrogen peroxide, 200 ppm azo-bis-(2-amidino-propene)dihydrochloride, 350 ppm sodiumpersulfate and then 100 ppm sodium erythorbate (all aqueous solutions) under adiabatic conditions and held near $T_{max}$ for 25 minutes. The resulting gel was chopped and extruded with a Hobarth 4M6 commercial extruder, followed by drying in a Procter & Schwartz Model 062 forced air oven at 175° C. for 10 minutes with upflow and 6 minutes with downflow air on a 20 in×40 in perforated metal tray to a final product moisture level of less than 5 wt %. The dried material was coarse ground in a Prodeva Model 315-S crusher, milled in an MPI 666-F three stage roller mill and sieved with an Minox MTS 600DS3V to remove particles greater than 850 microns and smaller than 150 microns. 400 g of the sieved powder was then blended uniformly with 0.5 wt % fumed alumina (Degussa Aluminumoxid C), followed by the uniform spray application of a solution containing 0.2 wt % aluminum sulfate, 0.1 wt % disodium cocoamphopropionate, 0.5 wt % tetraethyleneglycol dimethyl ether, and 1.0 wt % ethylene carbonate in 5 g of water, using a finely atomized spray while the SAP particles are fluidized in air. The coated material was then heated for 20 minutes at 180° C. in a General Signal/BM Model OV-510A-3 forced air oven.

Example 17

Similar to Example 16 except the sample was heated for 30 minutes at 180° C.

Example 18

Similar to Example 16 except the sample was heated for 40 minutes at 180° C.

Example 19

In an insulated, flat-bottomed reaction vessel, 1866.7 g of 50% NaOH was added to 3090.26 g of distilled water and cooled to 25° C. 800 g of acrylic acid was then added to caustic solution and the solution again cooled to 25° C. A second solution of 1600 g of acrylic acid containing 9.6 g of triallyamine, 120.53 g of 50 wt % methoxypolyethyleneglycol(750)monomethacrylate in acrylic acid and 7.2 g of trimethylolpropanetriacrylate with 9 moles of ethoxylation were then added to the first solution, followed by cooling to 15° C., the addition of 24.0 g of hydroxymonoallyl ether with 10 moles of ethoxylation, and additional cooling to 5° C., all while stirring. The monomer solution was then polymerized with a mixture of 150 ppm hydrogen peroxide, 200 ppm azo-bis-(2-amidino-propene)dihydrochloride, 350 ppm sodiumpersulfate and then 100 ppm sodium erythorbate (all aqueous solutions) under adiabatic conditions and held near $T_{max}$ for 25 minutes. The resulting gel was chopped and extruded with a Hobarth 4M6 commercial extruder, followed by drying in a Procter & Schwartz Model 062 forced air oven at 175° C. for 10 minutes with upflow and 6 minutes with downflow air on a 20 in×40 in perforated metal tray to a final product moisture level of less than 5 wt %. The dried material was coarse ground in a Prodeva Model 315-S crusher, milled in an MPI 666-F three stage roller mill and sieved with an Minox MTS 600DS3V to remove particles greater than 850 microns and smaller than 150 microns. 400 g of the sieved powder was then blended uniformly with 0.5 wt % fumed alumina (Degussa Aluminumoxid C), followed by the uniform spray application of a solution containing 0.2 wt % aluminum sulfate, 0.1 wt % disodium cocoamphopropionate, 0.5 wt % tetraethyleneglycol dimethyl ether, and 1.0 wt % ethylene carbonate in 5 g of water, using a finely atomized spray while the SAP particles are fluidized in air. The coated material was then heated for 20 minutes at 180° C. in a General Signal/BM Model OV-510A-3 forced air oven.

Example 20

Similar to Example 19 except the sample was heated for 30 minutes at 180° C.

Example 21

Similar to Example 19 except the sample was heated for 40 minutes at 180° C.

Example 22

In an insulated, flat-bottomed reaction vessel, 1866.7 g of 50% NaOH was added to 3090.26 g of distilled water and cooled to 25° C. 800 g of acrylic acid was then added to caustic solution and the solution again cooled to 25° C. A second solution of 1600 g of acrylic acid containing 4.2 g of triallyamine, 120.53 g of 50 wt % methoxypolyethyleneglycol(750)monomethacrylate in acrylic acid and 2.4 g of trimethylolpropanetriacrylate with 9 moles of ethoxylation were then added to the first solution, followed by cooling to 15° C., the addition of 24.0 g of hydroxymonoallyl ether with 10 moles of ethoxylation, and additional cooling to 5° C., all while stirring. The monomer solution was then polymerized with a mixture of 150 ppm hydrogen peroxide, 200 ppm azo-bis-(2-amidino-propene)dihydrochloride, 350 ppm sodiumpersulfate and then 100 ppm sodium erythorbate (all aqueous solutions) under adiabatic conditions and held near $T_{max}$ for 25 minutes. The resulting gel was chopped and extruded with a Hobarth 4M6 commercial extruder, followed by drying in a Procter & Schwartz Model 062 forced air oven at 175° C. for 10 minutes with upflow and 6 minutes with downflow air on a 20 in×40 in perforated metal tray to a final product moisture level of less than 5 wt %. The dried material was coarse ground in a Prodeva Model 315-S crusher, milled in an MPI 666-F three stage roller mill and sieved with an Minox MTS 600DS3V to remove particles greater than 850 microns and smaller than 150 microns. 400 g of the sieved powder was then blended uniformly with 0.5 wt % fumed alumina (Degussa Aluminumoxid C), followed by the uniform spray application of a solution containing 0.2 wt % aluminum sulfate, 0.1 wt % disodium cocoamphopropionate, 0.5 wt % tetraethyleneglycol dimethyl ether, and 1.0 wt % ethylene carbonate in 5 g of water, using a finely atomized spray while the SAP particles are fluidized in air. The coated material was then heated for 20 minutes at 180° C. in a General Signal/BM Model OV-510A-3 forced air oven.

Example 23

Similar to Example 22 except the sample was heated for 30 minutes at 180° C.

Example 24

Similar to Example 22 except the sample was heated for 40 minutes at 180° C.

Example 25

In an insulated, flat-bottomed reaction vessel, 1866.7 g of 50% NaOH was added to 3090.26 g of distilled water and cooled to 25° C. 800 g of acrylic acid was then added to caustic solution and the solution again cooled to 25° C. A second solution of 1600 g of acrylic acid containing 9.6 g of polyethylene glycol (300) diacrylate was then added to the first solution, followed by cooling to 15° C., the addition of 9.6 g of monoallyl ether acrylate with 10 moles of ethoxylation, and additional cooling to 5° C., all while stirring. The monomer solution was then polymerized with a mixture of 100 ppm hydrogen peroxide, 200 ppm azo-bis-(2-amidinopropene)dihydrochloride, 200 ppm sodiumpersulfate and then 40 ppm ascorbic acid (all aqueous solutions) under adiabatic conditions and held near $T_{max}$ for 25 minutes. The resulting gel was chopped and extruded with a Hobarth 4M6 commercial extruder, followed by drying in a Procter & Schwartz Model 062 forced air oven at 175° C. for 10 minutes with upflow and 6 minutes with downflow air on a 20 in×40 in perforated metal tray to a final product moisture level of less than 5 wt %. The dried material was coarse ground in a Prodeva Model 315-S crusher, milled in an MPI 666-F three stage roller mill and sieved with an Minox MTS 600DS3V to remove particles greater than 850 microns and smaller than 150 microns. 400 g of the sieved powder was then blended uniformly with 0.05 wt % kaolin (Neogen DGH), followed by the uniform spray application of a solution containing 0.5 wt % aluminum sulfate, 0.3 wt % N2-hydroxyethyl-N2-carboxyethylcocoamidoethyl amine sodium salt, and 1.0 wt % ethylene carbonate in 12 g of water, using a finely atomized spray while the SAP particles are fluidized in air. The coated material was then heated for 25 minutes at 186° C. in an electrically heated paddle drier.

Example 26

Similar to Example 25 except 12.0 g of polyethylene glycol (300) diacrylate and 12.0 g of monoallyl ether acrylate with 10 moles of ethoxylation were used in the monomer solution.

Example 27

In an insulated, flat-bottomed reaction vessel, 1866.7 g of 50% NaOH was added to 3090.26 g of distilled water and cooled to 25° C. 800 g of acrylic acid was then added to caustic solution and the solution again cooled to 25° C. A second solution of 1600 g of acrylic acid containing 9.6 g of polyethylene glycol (300) diacrylate was then added to the first solution, followed by cooling to 15° C., the addition of 9.6 g of monoallyl ether acrylate with 10 moles of ethoxylation, and additional cooling to 5° C., all while stirring. The monomer solution was then polymerized with a mixture of 100 ppm hydrogen peroxide, 200 ppm azo-bis-(2-amidinopropene)dihydrochloride, 200 ppm sodiumpersulfate and 40 ppm ascorbic acid (all aqueous solutions) under adiabatic conditions and held near $T_{max}$ for 25 minutes. The resulting gel was chopped and extruded with a Hobarth 4M6 commercial extruder, followed by drying in a Procter & Schwartz Model 062 forced air oven at 175° C. for 10 minutes with upflow and 6 minutes with downflow air on a 20 in×40 in perforated metal tray to a final product moisture level of less than 5 wt %. The dried material was coarse ground in a Prodeva Model 315-S crusher, milled in an MPI 666-F three stage roller mill and sieved with an Minox MTS 600DS3V to remove particles greater than 850 microns and smaller than 150 microns. 400 g of the sieved powder was then blended uniformly with 0.2 wt % kaolin (Neogen DGH), followed by the uniform spray application of a solution containing 0.5 wt % aluminum sulfate, and 1.0 wt % ethylene carbonate in 12 g of water, using a finely atomized spray while the SAP particles are fluidized in air. The coated material was then heated for 25 minutes at 186° C. in an electrically heated paddle drier.

Example 28

Similar to Example 27 except 12.0 g of polyethylene glycol (300) diacrylate and 12.0 g of monoallyl ether acrylate with 10 moles of ethoxylation were used in the monomer solution.

Example 29

In an insulated, flat-bottomed reaction vessel, 1866.7 g of 50% NaOH was added to 3090.26 g of distilled water and cooled to 25° C. 800 g of acrylic acid was then added to caustic solution and the solution again cooled to 25° C. A second solution of 1600 g of acrylic acid containing 120 g of 50 wt % methoxypolyethyleneglycol(750)monomethacrylate in acrylic acid and 6.0 g of trimethylolpropanetriacrylate with 3 moles of ethoxylation were then added to the first solution, followed by cooling to 15° C., the addition of 10.8 g of allyl ether acrylate with 10 moles of ethoxylation, and additional cooling to 5° C., all while stirring. The monomer solution was then polymerized with a mixture of 100 ppm hydrogen peroxide, 125 ppm azo-bis-(2-amidino-propene) dihydrochloride, 300 ppm sodiumpersulfate and 30 ppm sodium erythorbate (all aqueous solutions) under adiabatic conditions and held near $T_{max}$ for 25 minutes. The resulting gel was chopped and extruded with a Hobarth 4M6 commercial extruder, followed by drying in a Procter & Schwartz Model 062 forced air oven at 175° C. for 10 minutes with upflow and 6 minutes with downflow air on a 20 in×40 in perforated metal tray to a final product moisture level of less than 5 wt %. The dried material was coarse ground in a Prodeva Model 315-S crusher, milled in an MPI 666-F three stage roller mill and sieved with an Minox MTS 600DS3V to remove particles greater than 850 microns and smaller than 150 microns. 400 g of the sieved powder was then blended uniformly with 0.5 wt % fumed alumina (Degussa Aluminumoxid C), followed by the uniform spray application of a solution containing 0.2 wt % aluminum sulfate, 0.1 wt % disodium cocoamphopropionate, 0.5 wt % tetraethyleneglycol dimethyl ether, and 1.0 wt % ethylene carbonate in 5 g of water, using a finely atomized spray while the SAP particles are fluidized in air. The coated material was then heated for 20 minutes at 180° C. in a General Signal/BM Model OV-510A-3 forced air oven.

Example 30

In an insulated, flat-bottomed reaction vessel, 1866.7 g of 50% NaOH was added to 3090.26 g of distilled water and cooled to 25° C. 800 g of acrylic acid was then added to caustic solution and the solution again cooled to 25° C. A second solution of 1600 g of acrylic acid containing 120 g of 50 wt % methoxypolyethyleneglycol(750)monomethacrylate in acrylic acid and 14.4 g of trimethylolpropanetriacrylate with 3 moles of ethoxylation were then added to the first solution, followed by cooling to 15° C., the addition of 14.4 g of hydroxymonoallyl ether with 10 moles of ethoxylation, and additional cooling to 5° C., all while stirring. The monomer solution was then polymerized with a mixture of 100 ppm hydrogen peroxide, 200 ppm azo-bis-(2-amidino-propene) dihydrochloride, 200 ppm sodiumpersulfate and 40 ppm ascorbic acid (all aqueous solutions) under adiabatic conditions and held near $T_{max}$ for 25 minutes. The resulting gel was chopped and extruded with a Hobarth 4M6 commercial extruder, followed by drying in a Procter & Schwartz Model 062 forced air oven at 175° C. for 10 minutes with upflow and 6 minutes with downflow air on a 20 in×40 in perforated metal tray to a final product moisture level of less than 5 wt %. The dried material was coarse ground in a Prodeva Model 315-S crusher, milled in an MPI 666-F three stage roller mill and sieved with an Minox MTS 600DS3V to remove particles greater than 850 microns and smaller than 150 microns. 400 g of the sieved powder was then blended uniformly with 0.5 wt % fumed silica Aerosil 200 followed by the uniform spray application of a solution containing 0.01 wt % aluminum sulfate and 1.0 wt % ethylene carbonate in 4 g of water, using a finely atomized spray while the SAP particles are fluidized in air. The coated material was then heated for 135 minutes at 176° C. in an electrically heated paddle drier.

Example 31

In an insulated, flat-bottomed reaction vessel, 1866.7 g of 50% NaOH was added to 3090.26 g of distilled water and cooled to 25° C. 800 g of acrylic acid was then added to caustic solution and the solution again cooled to 25° C. A second solution of 1600 g of acrylic acid containing 120 g of 50 wt % methoxypolyethyleneglycol(750)monomethacrylate in acrylic acid and 6.0 g of trimethylolpropanetriacrylate with 3 moles of ethoxylation were then added to the first solution, followed by cooling to 15° C., the addition of 10.8 g of hydroxymonoallyl ether with 10 moles of ethoxylation, and additional cooling to 5° C., all while stirring. The monomer solution was then polymerized with a mixture of 100 ppm hydrogen peroxide, 125 ppm azo-bis-(2-amidino-propene) dihydrochloride, 300 ppm sodiumpersulfate and then 30 ppm sodium erythorbate (all aqueous solutions) under adiabatic conditions and held near $T_{max}$ for 25 minutes. The resulting gel was chopped and extruded with a Hobarth 4M6 commercial extruder, followed by drying in a Procter & Schwartz Model 062 forced air oven at 175° C. for 10 minutes with upflow and 6 minutes with downflow air on a 20 in×40 in perforated metal tray to a final product moisture level of less than 5 wt %. The dried material was coarse ground in a Prodeva Model 315-S crusher, milled in an MPI 666-F three stage roller mill and sieved with an Minox MTS 600DS3V to remove particles greater than 850 microns and smaller than 150 microns. 400 g of the sieved powder was then blended uniformly with 0.5 wt % fumed silica Aerosil 200 and 1.0 wt % kaolin (Neogen DGH), followed by the uniform spray application of a solution containing 0.01 wt % aluminum sulfate, and 1.0 wt % ethylene carbonate in 4 g of water, using a finely atomized spray while the SAP particles are fluidized in air. The coated material was then heated for 135 minutes at 175° C. in a General Signal/BM Model OV-510A-3 forced air oven.

TABLE 1

| | CRC (g/g) | GBP (×10-9 cm$^2$) | G' (dynes/cm$^2$) | AAP (g/g) |
|---|---|---|---|---|
| Example 1 | 29 | 661 | 5568 | 19.3 |
| Example 2 | 27.6 | 910 | 6386 | 20.4 |
| Example 3 | 26.9 | 927 | 7746 | 20.1 |
| Example 4 | 27 | 1194 | 6183 | 21.5 |
| Example 5 | 25.1 | 1252 | 8436 | 22.0 |
| Example 6 | 24 | 1589 | 8797 | 22.1 |
| Example 7 | 30.1 | 554 | 6011 | 19.1 |
| Example 8 | 27.8 | 928 | 7966 | 21.2 |
| Example 9 | 26 | 1100 | 7999 | 21.4 |
| Example 10 | 28.3 | 675 | 4248 | 18.9 |
| Example 11 | 24.4 | 2039 | 6463 | 21.9 |
| Example 12 | 23.1 | 1852 | 7312 | 22.2 |
| Example 13 | 28.4 | 947 | 4472 | 19.1 |
| Example 14 | 25.8 | 1510 | 4639 | 19.5 |
| Example 15 | 24.2 | 2132 | 5536 | 20.4 |
| Example 16 | 31.3 | 647 | 4813 | 19.7 |
| Example 17 | 27.7 | 1055 | 5497 | 20.1 |
| Example 18 | 26.4 | 1457 | 6110 | 21.1 |
| Example 19 | 30.2 | 457 | 3484 | 18.5 |
| Example 20 | 29.6 | 592 | 4275 | 20.5 |
| Example 21 | 27.9 | 945 | 5017 | 20.1 |
| Example 22 | 32.2 | 382 | 3890 | 19.6 |
| Example 23 | 28.1 | 1091 | 5222 | 21.0 |
| Example 24 | 26.5 | 1278 | 5862 | 20.5 |
| Example 25 | 32 | 390 | 6227 | 20.3 |
| Example 26 | 30 | 500 | 6797 | 21.5 |
| Example 27 | 30 | 612 | 6899 | 21.2 |
| Example 28 | 29 | 862 | 7777 | 22.4 |
| Example 29 | 31 | 836 | 5182 | 19.7 |
| Example 30 | 27.8 | 1456 | 6872 | 20.8 |
| Example 31 | 31 | 736 | 6011 | 19.4 |

TABLE 2

Existing Art Superabsorbent Polymers

| | CRC (g/g) | G' (dynes/cm2) | GBP | AAP (0.7 psi) |
|---|---|---|---|---|
| Sanwet 770H | 32.4 | 4305 | 58 | 22.3 |
| Hy-Sorb M 7055 | 33.1 | 4276 | 55 | 24.2 |
| Hysorb 100 | 26.3 | 5649 | 95 | 24 |
| BASF 2300 | 33.4 | 4034 | 58 | 19.7 |
| BASF 7050 | 31.1 | 5033 | 62 | 26.5 |
| BASF 2260 | 23.9 | 9025 | 553 | 19.5 |
| BASF ASAP 2000 | 31.4 | 3688 | 50 | 21 |
| Sumitumo SA60 | 32.5 | 3196 | 37 | 13 |
| Kolon GS3400 | 30.4 | 6818 | 186 | 22.6 |
| Kolon GS3000 | 38.9 | 2811 | 20 | 22 |
| DryTech 2035M | 30.4 | 7138 | 35 | 15.1 |
| DOW S100R | 28.2 | 6032 | 88 | 24.3 |
| Aqualic CAB | 34.4 | 3356 | 176 | 17.4 |
| SAP from Pampers Baby Dry diapers | 28.4 | 5746 | 143 | 20.6 |
| SAP from Pampers Premium diapers | 30.8 | 5573 | 130 | 23.3 |
| SAP from Pampers Cruisers | 28.9 | 6866 | 154 | 22.2 |
| SAP from Luv's diapers | 27.3 | 6954 | 137 | 22.0 |
| SAP from Huggies UltraTrim diaper | 21.5 | 11490 | 408 | 20.9 |
| SAP from Huggies Overnites | 29.6 | 6889 | 110 | 10.5 |
| SAP from Huggies Supremes | 22.2 | 11360 | 325 | 18.0 |
| SAP from White Cloud diaper | 22.1 | 9785 | 435 | 14.4 |
| SAP from White Cloud training pants | 22.3 | 9490 | 373 | 13.3 |
| SAP from Walgreens UltraValue diapers | 26.9 | 7590 | 278 | 15.9 |
| SAP from DriBottoms diapers | 22.4 | 9545 | 273 | 14.4 |
| SAP recovered from PaperPak Adult Briefs | 39.5 | 4554 | 10 | 13.1 |

FIG. 4 shows the typical relationship between retention as measured by centrifuge retention capacity and permeability as measured by GBP can be described approximately by GBP=$54000e^{-0.2275x}$, where x=CRC. Permeabilities greater than $500\times10^{-9}$ cm$^2$ are only achieved at very low retention values, that is CRCs of less than about 25 g/g. In the present invention, FIG. 4 shows an entirely different relationship exists between centrifuge retention capacity and permeability as measured as GBP. FIG. 4 shows much higher permeability at much higher CRC values. The permeability is often double, triple or even quadruple what was shown for prior art.

Figure 5:
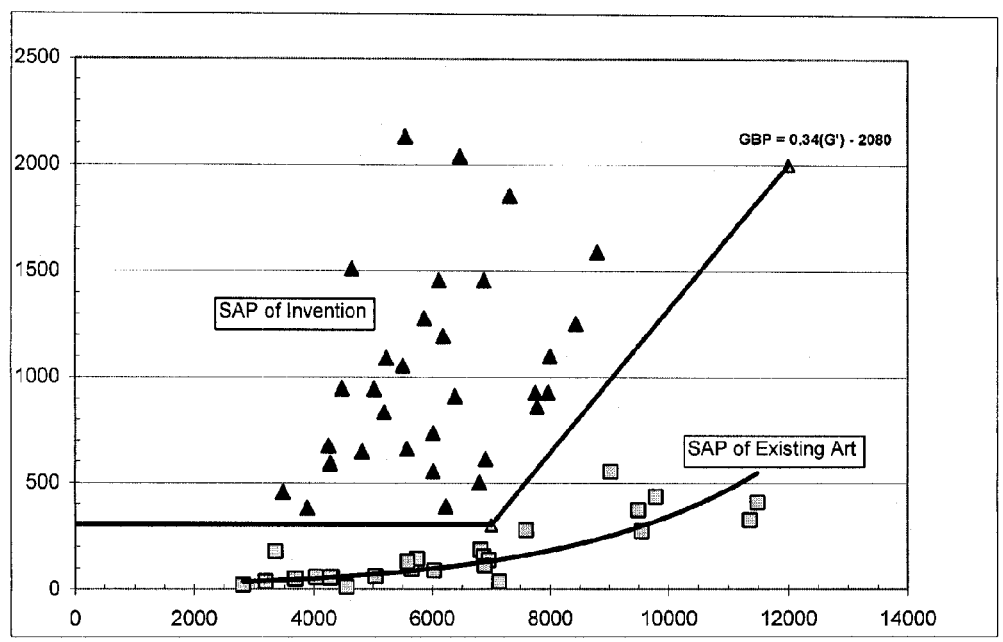
FIG. 5 is a graph depicting the relationship of Gel Bed Permeability GBP and Shear Modulus G'.

FIG. 5 illustrates the difference in SAP's made using the current art and SAP's made by the present invention with respect to the relationship between the permeability and the shear modulus. The present invention combines much higher values of gel bed permeabilities, GBP, at lower gel strengths than previously available materials.

The examples described for the process according to the invention all show a very good overall performance, in particular in respect to the relationship of retention and permeability. Free-flowing coated powders that can easily be metered are obtained.

What is claimed:

1. A particulate superabsorbent polymer composition comprising:
    a) from about 55 to about 99.9 wt. % of a monomer, which contain carboxyl groups including acrylic acid, methacrylic acid, or mixtures of these monomers wherein the monomer is neutralized to from 50 to 80 mol %;
    b) from about 0.001 to about 3.0 wt. % based on the weight of a) of internal crosslinking agent;
    wherein elements a) and b) are polymerized into a polymer gel which is then dried in a forced air oven to have a moisture content of less than 5 wt %, and comminuted into particulate superabsorbent polymer composition having a particle size of from 150 to 850 μm and a particle surface and further comprising
    c) from about 0.001 to about 5.0 wt. % based on a dry polymer powder weight of an alkylene carbonate applied to the particle surface in a surface crosslinking step;
    d) from about 0.01% to about 5 wt. % based on the dry polymer powder weight of polyethylene glycol or tetraethyleneglycol dimethylether added immediately prior to or during the surface crosslinking step;
    e) from about 0.01 wt. % to about 5 wt. % based on the dry polymer powder weight of a multivalent metal salt selected from aluminum sulfate on the particle surface;
    f) from about 0.01 to about 5 wt % based on the dry polymer powder weight of a water-insoluble, inorganic powder selected from kaolin, silicon dioxide, fumed silica, silicic acid, silicates, titanium dioxide, aluminum oxide, fumed alumina, calcium phosphate, or clays; and
    g) from about 0.1 to about 0.3 wt % based on the dry polymer powder weight of a surfactant selected from disodium cocoamphopropionate or cocomonoethanol amide with 4.5 moles ethoxylation;
    wherein the composition has a degree of neutralization of more than about 25%; and a Centrifuge Retention Capacity of from about 23 g/g to about 40 g/g as determined by the Centrifuge Retention Capacity Test set forth herein and a gel bed permeability of from about $400\times10^{-9}$ cm$^2$ to about $2500\times10^{-9}$ cm$^2$ as determined by the Gel Bed Permeability Test set forth herein.

2. The particulate superabsorbent polymer composition according to claim 1 wherein the gel bed permeability is from about $500\times10^{-9}$ cm$^2$ to about $2000\times10^{-9}$ cm$^2$.

3. The particulate superabsorbent polymer composition according to claim 1 wherein the gel bed permeability is from about $800\times10^{-9}$ cm$^2$ to about $1500\times10^{-9}$ cm$^2$.

4. The particulate superabsorbent polymer composition according to claim 1 wherein the Centrifuge Retention Capacity is from about 25 g/g to about 35 g/g as determined by the Centrifuge Retention Capacity Test set forth herein.

5. A water insoluble, slightly cross-linked, partially neutralized, particulate superabsorbent polymer composition having a particle size of from 150 to 850 μm and a particle surface and comprising a monomer which contain carboxyl groups including acrylic acid, methacrylic acid, or mixtures of these monomers and an internal crosslinking agent, and the water insoluble, slightly cross-linked, partially neutralized, particulate superabsorbent polymer wherein the slightly cross-linked, partially neutralized, particulate superabsorbent polymer is dried in a forced air oven to have a moisture content of less than 5 wt %, the slightly cross-linked, partially neutralized, particulate superabsorbent polymer further comprising a polyethylene glycol or tetraethyleneglycol dimethylether; from about 0.1 to about 0.3 wt % based on the dry polymer powder weight of a surfactant selected from disodium cocoamphopropionate or cocomonoethanol amide with 4.5 moles ethoxylation; a water-insoluble inorganic powder selected from kaolin, fumed silica, or fumed alumina, and a multivalent metal salt selected from aluminum sulfate, wherein the particulate superabsorbent polymer has a Centrifuge Retention Capacity of from about 23 g/g to about 40 g/g as determined by the Centrifuge Retention Capacity Test set forth herein and a Gel Bed Permeability of from about $500\times10^{-9}$ cm$^2$ to about $2500\times10^{-9}$ cm$^2$ as determined by the Gel Bed Permeability Test set forth herein.

6. The water insoluble, slightly cross-linked, partially neutralized, particulate superabsorbent polymer composition according to claim 5 wherein the gel bed permeability is from about $800\times10^{-9}$ cm$^2$ to about $1500\times10^{-9}$ cm$^2$.

7. The water insoluble, slightly cross-linked, partially neutralized, particulate superabsorbent polymer composition according to claim 5 wherein the Centrifuge Retention Capacity is from about 30 g/g to about 40 g/g.

8. The water insoluble, slightly cross-linked, partially neutralized, particulate superabsorbent polymer composition according to claim 5 having the characteristics of Centrifuge Retention Capacity from about 30 g/g to about 36 g/g; and a gel bed permeability from about $600\times10^{-9}$ cm$^2$ to about $800\times10^{-9}$ cm$^2$.

9. A particulate superabsorbent polymer composition comprising:
    a) from about 55 to about 99.9 wt. % of a monomer, which contain carboxyl groups including acrylic acid, methacrylic acid, or mixtures of these monomers wherein the monomer is neutralized to from 50 to 80 mol %;
    b) from about 0.001 to about 3.0 wt. % based on the weight of a) of internal crosslinking agent selected from triallylamine, trimethylolpropanetriacrylate with 9 moles of ethoxylation, allyl ether acrylate with 10 moles of ethoxylation, polyethylene glycol (300)diacrylate, trimethylolpropanetriacrylate with 3 moles of ethoxylation, or mixtures thereof;
    wherein elements a) and b) are polymerized, then dried in a forced air oven to have a moisture content of less than 5 wt %, and comminuted into said superabsorbent polymer particulate having a particle size of from 150 to 850 μm, which includes a particle surface, wherein the particulate superabsorbent polymer further comprises of c) from about 0.001 to about 5.0 wt. % based on dry polymer powder weight of an alkylene carbonate applied to the particle surface in a surface crosslinking step;

d) from about 0.01% to about 5 wt. % based on dry polymer powder weight of polyethylene glycol or tetraethyleneglycol dimethylether added immediately prior to or during the surface crosslinking step;

e) from about 0.01 wt % to about 5 wt. % based on dry polymer powder weight of a multivalent metal salt on the surface wherein the multivalent metal salt is selected from aluminum sulfate;

f) from about 0.01 to about 5 wt % based on dry polymer powder weight of a water-insoluble, inorganic powder selected from kaolin, fumed silica, or fumed alumina, and g) from about 0.1 to about 0.3 wt % based on the dry polymer powder weight of a surfactant selected from disodium cocoamphopropionate or cocomonoethanol amide with 4.5 moles ethoxylation;

wherein said superabsorbent polymer particulate having the characteristics of Centrifuge Retention Capacity from about 30 to about 40 g/g as determined by the Centrifuge Retention Capacity Test set forth herein, and a Gel Bed Permeability of about $400 \times 10^{-9}$ cm$^2$ or more as determined by the Gel Bed Permeability Test set forth herein.

10. The particulate superabsorbent polymer composition according to claim 9 where the gel bed permeability is from about $500 \times 10^{-9}$ cm$^2$ to about $2000 \times 10^{-9}$ cm$^2$.

11. The particulate superabsorbent polymer composition as set forth in claim 1 having a Centrifuge Retention Capacity as determined by the Centrifuge Retention Capacity Test of at least from about 24 g/g to about 32 g/g.

12. The particulate superabsorbent polymer composition as set forth in claim 1 having a Centrifuge Retention Capacity as determined by the Centrifuge Retention Capacity Test of from about 30 g/g to about 40 g/g.

13. The particulate superabsorbent polymer composition as set forth in claim 1 having an Absorption Against Pressure at 0.7 psi as determined by an Absorption Against Pressure Test of from about 18 to about 23 g/g.

14. A particulate superabsorbent polymer composition a) comprising a crosslinked superabsorbent polymer or combination of polymers comprising from about 55 to about 99.9 weight percent of polymerizable unsaturated acid group containing monomers which are selected from acrylic acid, methacrylic acid, or mixtures of these wherein the monomer is neutralized to from 50 to 80 mol % and ethylenically unsaturated monomers selected from acrylamidopropyltrimethylammonium chloride and ethoxylated (meth)-acrylates, and b) a crosslinking agent wherein the particulate superabsorbent polymer composition further comprises from about 0.1 to about 0.3 wt % based on the dry polymer powder weight of a surfactant selected from disodium cocoamphopropionate or cocomonoethanol amide with 4.5 moles ethoxylation, wherein the particulate superabsorbent polymer composition is dried in a forced air oven to have a moisture content of less than 5 wt %, a Centrifuge Retention Capacity as determined by a Centrifuge Retention Capacity Test of at least about 25 g/g, an Absorption Against Pressure at 0.7 psi as determined by an Absorption Against Pressure Test of less than about 23 g/g and a free swell gel bed permeability (GBP) as determined by a Free Swell Gel Bed Permeability Test of at least about $400 \times 10^{-9}$ cm$^2$.

15. The particulate superabsorbent polymer composition as set forth in claim 14 having a swell gel bed permeability as determined by the Free Swell Gel Bed Permeability Test of at least about $600 \times 10^{-9}$ cm$^2$.

16. The particulate superabsorbent polymer composition as set forth in claim 14 having a Centrifuge Retention Capacity as determined by the Centrifuge Retention Capacity Test of at least about 27 g/g.

17. The particulate superabsorbent polymer composition as set forth in claim 14 having a Centrifuge Retention Capacity as determined by the Centrifuge Retention Capacity Test of at least about 30 g/g.

18. The particulate superabsorbent polymer composition as set forth in claim 14 further comprising at least one of: from about 0.001 to about 5.0 weight percent of an internal crosslinking agent; from about 0.001 to about 5.0 weight percent of a surface crosslinking agent applied to the surface of the superabsorbent polymer; from about 0.01% to about 5 wt. % based on dry polymer powder weight of a penetration modifier applied to the surface of the superabsorbent polymer; up to about 5 weight percent of a multivalent metal salt selected from aluminum sulfate on the surface of the superabsorbent polymer; from about 0.01 to about 5 weight percent of a water-insoluble, inorganic powder; and from about 0.1 to about 0.3 wt % based on the dry polymer powder weight of a surfactant on the surface of the superabsorbent polymer.

19. The particulate superabsorbent polymer composition as set forth in claim 14 having a degree of neutralization of more than about 50 mol percent.

20. The particulate superabsorbent polymer composition as set forth in claim 14 further comprising at least one of: from about 0.001 to about 5.0 weight percent of an internal crosslinking agent; from about 0.001 to about 5.0 weight percent of a surface crosslinking agent applied to the surface of the superabsorbent polymer; from about 0.01% to about 5 wt. % based on dry polymer powder weight of polyethylene glycol or tetraethyleneglycol dimethylether applied to the surface of the superabsorbent polymer; up to about 5 weight percent of a multivalent metal salt selected from aluminum sulfate on the surface of the superabsorbent polymer; from about 0.01 to about 5 weight percent of a water-insoluble, inorganic powder selected from kaolin, fumed silica, or fumed alumina; and from about 0.1 to about 0.3 wt % based on the dry polymer powder weight of a surfactant on the surface of the superabsorbent polymer.

21. A particulate superabsorbent polymer composition comprising a crosslinked superabsorbent polymer or combination of polymers comprising a) from about 55 to about 99.9 weight percent of polymerizable unsaturated acid group containing monomers and ethylenically unsaturated monomers which can be copolymerized with the polymerizable unsaturated acid group containing monomers and which are selected from acrylamidopropyltrimethylammonium chloride and ethoxylated (meth)-acrylates, and b) a crosslinking agent wherein the particulate superabsorbent polymer composition further comprises from about 0.1 to about 0.3 wt % based on the dry polymer powder weight of a surfactant selected from disodium cocoamphopropionate or cocomonoethanol amide with 4.5 moles ethoxylation, and wherein the superabsorbent material is dried in a force air oven to have a moisture content of less than 5 wt %, a Centrifuge Retention Capacity as determined by a Centrifuge Retention Capacity Test of from about 27 g/g to about 40 g/g, an Absorption Against Pressure at 0.7 psi as determined by an Absorption Against Pressure Test of from about 18 g/g to about 23 g/g and a free swell gel bed permeability as determined by a Free Swell Gel Bed Permeability Test of from about $400 \times 10^{-9}$ cm$^2$ to about $2000 \times 10^{-9}$ cm$^2$.

\* \* \* \* \*